(12) United States Patent     (10) Patent No.:   US 12,667,314 B2

Sampson     (45) Date of Patent:   *Jun. 30, 2026

(54) SYSTEM AND METHOD TO DETECT CHANGES IN HEALTH PARAMETERS AND ACTIVATE LIFESAVING MEASURES

(71) Applicant: Sherlock Solutions LLC, Stony Brook, NY (US)

(72) Inventor: Robert Sampson, Stony Brook, NY (US)

(73) Assignee: SHERLOCK SOLUTIONS LLC, Stony Brook, NY (US)

(*) Notice: Subject to any disclaimer, the term of this patent is extended or adjusted under 35 U.S.C. 154(b) by 713 days.

This patent is subject to a terminal disclaimer.

(21) Appl. No.: 17/853,083

(22) Filed: Jun. 29, 2022

(65) Prior Publication Data

US 2022/0401035 A1    Dec. 22, 2022

Related U.S. Application Data

(63) Continuation of application No. 16/687,344, filed on Nov. 18, 2019, now Pat. No. 11,406,329, which is a
(Continued)

(51) Int. Cl.
    *A61B 5/00*       (2006.01)
    *A61B 5/0205*     (2006.01)
    (Continued)

(52) U.S. Cl.
    CPC ............ *A61B 5/721* (2013.01); *A61B 5/0022* (2013.01); *A61B 5/0205* (2013.01);
    (Continued)

(58) Field of Classification Search
    CPC . A61B 5/0022; A61B 5/0205; A61B 5/02438; A61B 5/0261; A61B 5/14551;
         (Continued)

(56) References Cited

U.S. PATENT DOCUMENTS

| 3,832,994 A | 9/1974 | Bicher et al. |
| 5,351,695 A | 10/1994 | Mills et al. |
| | (Continued) | |

FOREIGN PATENT DOCUMENTS

| KR | 20130010207 A | 1/2013 |
| WO | 2013165474 A1 | 11/2013 |

OTHER PUBLICATIONS

Curone, et al. "Heart rate and accelerometer data fusion for activity assessment of rescuers during emergency interventions." IEEE Transactions on Information Technology in Biomedicine 14.3 (2010): 702-710.

(Continued)

*Primary Examiner* — Benjamin J Klein

(74) *Attorney, Agent, or Firm* — NORTON ROSE FULBRIGHT US LLP

(57) ABSTRACT

Certain exemplary embodiments can provide an apparatus wearable by a user. The apparatus can comprise a biometric sensor constructed to generate signals based upon measurements of the user. The apparatus can comprise a processor constructed to determine a significant detrimental change in the user via an algorithm based upon the signals.

20 Claims, 12 Drawing Sheets

Related U.S. Application Data continuation of application No. 14/748,230, filed on Jun. 23, 2015, now Pat. No. 10,478,127.

(60) Provisional application No. 62/015,844, filed on Jun. 23, 2014.

(51) Int. Cl.

| | |
|---|---|
| *A61B 5/024* | (2006.01) |
| *A61B 5/026* | (2006.01) |
| *A61B 5/1455* | (2006.01) |
| *A61B 5/282* | (2021.01) |
| *A61B 5/366* | (2021.01) |
| *G16H 40/63* | (2018.01) |

(52) U.S. Cl.
CPC ........ *A61B 5/0261* (2013.01); *A61B 5/14551* (2013.01); *A61B 5/282* (2021.01); *A61B 5/6803* (2013.01); *A61B 5/681* (2013.01); *A61B 5/7221* (2013.01); *A61B 5/7264* (2013.01); *A61B 5/7275* (2013.01); *A61B 5/7282* (2013.01); *A61B 5/746* (2013.01); *A61B 5/7475* (2013.01); *G16H 40/63* (2018.01); *A61B 5/02438* (2013.01); *A61B 5/366* (2021.01); *A61B 5/7203* (2013.01); *A61B 2560/0228* (2013.01)

(58) Field of Classification Search
CPC ......... A61B 5/282; A61B 5/291; A61B 5/366; A61B 5/6803; A61B 5/681; A61B 5/7203; A61B 5/721; A61B 5/7221; A61B 5/7264; A61B 5/7275; A61B 5/7282; A61B 5/746; A61B 5/7475; A61B 2560/0228; G16H 40/63
See application file for complete search history.

(56) References Cited

U.S. PATENT DOCUMENTS

| | | | |
|---|---|---|---|
| 5,515,858 | A | 5/1996 | Myllymaki |
| 7,869,864 | B2 | 1/2011 | Tseng et al. |
| 7,894,888 | B2 | 2/2011 | Chan et al. |
| 8,055,331 | B2 | 11/2011 | Satin et al. |
| 8,332,020 | B2 | 12/2012 | Zdeblick |
| 8,626,274 | B2 | 1/2014 | Chiu et al. |
| 8,738,118 | B2 | 5/2014 | Moon et al. |
| 9,041,530 | B2 | 5/2015 | Sprigg et al. |
| 9,317,110 | B2 | 4/2016 | Lutnick et al. |
| 10,051,410 | B2 | 8/2018 | Booth et al. |
| 10,478,127 | B2 | 11/2019 | Sampson |
| 10,534,819 | B2 | 1/2020 | Ricci |
| 2004/0130446 | A1 | 7/2004 | Chen et al. |
| 2005/0116810 | A1 | 6/2005 | Beenau et al. |
| 2006/0052983 | A1 | 3/2006 | Vock et al. |
| 2006/0152373 | A1 | 7/2006 | King |
| 2006/0161065 | A1 | 7/2006 | Elion |
| 2006/0281996 | A1 | 12/2006 | Kuo et al. |
| 2007/0116330 | A1 | 5/2007 | Takiguchi |
| 2007/0276270 | A1 | 11/2007 | Tran |
| 2008/0004904 | A1 | 1/2008 | Tran |
| 2009/0048526 | A1 | 2/2009 | Aarts et al. |
| 2009/0105558 | A1 | 4/2009 | Riley-Doucet et al. |
| 2009/0131759 | A1 | 5/2009 | Sims et al. |
| 2009/0322513 | A1 | 12/2009 | Hwang et al. |
| 2010/0076331 | A1 | 3/2010 | Chan et al. |
| 2010/0249542 | A1 | 9/2010 | Thijs et al. |
| 2011/0004072 | A1 | 1/2011 | Fletcher et al. |
| 2011/0066009 | A1 | 3/2011 | Moon et al. |
| 2011/0066010 | A1 | 3/2011 | Moon et al. |
| 2012/0002791 | A1 | 1/2012 | Kraus et al. |
| 2012/0092157 | A1 | 4/2012 | Tran |
| 2012/0150244 | A1 | 6/2012 | Freeman et al. |
| 2012/0330109 | A1 | 12/2012 | Tran |
| 2013/0009783 | A1 | 1/2013 | Tran |
| 2013/0072807 | A1 | 3/2013 | Tran |
| 2013/0083009 | A1 | 4/2013 | Geisner et al. |
| 2013/0178755 | A1 | 7/2013 | Waters |
| 2013/0211291 | A1 | 8/2013 | Tran |
| 2013/0231574 | A1 | 9/2013 | Tran |
| 2013/0231578 | A1 | 9/2013 | Takayanagi et al. |
| 2013/0281816 | A1 | 10/2013 | Strauss et al. |
| 2013/0307685 | A1 | 11/2013 | Sholder |
| 2013/0345578 | A1 | 12/2013 | Nadkarni et al. |
| 2014/0058280 | A1 | 2/2014 | Chefles et al. |
| 2014/0077946 | A1 | 3/2014 | Tran |
| 2014/0104059 | A1 | 4/2014 | Tran |
| 2014/0107457 | A1 | 4/2014 | Raghunathan |
| 2014/0142403 | A1 | 5/2014 | Brumback et al. |
| 2014/0163425 | A1 | 6/2014 | Tran |
| 2014/0247154 | A1 | 9/2014 | Proud |
| 2014/0249429 | A1 | 9/2014 | Tran |
| 2014/0277582 | A1 | 9/2014 | Leuthardt et al. |
| 2014/0288391 | A1 | 9/2014 | Hong et al. |
| 2014/0310186 | A1 | 10/2014 | Ricci |
| 2015/0025394 | A1 | 1/2015 | Hong et al. |
| 2015/0049114 | A1 | 2/2015 | Geisner et al. |
| 2015/0068069 | A1 | 3/2015 | Bach et al. |
| 2015/0094914 | A1 | 4/2015 | Abreu |
| 2015/0257654 | A1 | 9/2015 | Bennett-Guerrero |
| 2015/0279187 | A1 | 10/2015 | Kranz |
| 2015/0285659 | A1 | 10/2015 | Curtis et al. |
| 2015/0317515 | A1 | 11/2015 | Lake et al. |
| 2015/0351698 | A1 | 12/2015 | Cronin |
| 2015/0366518 | A1 | 12/2015 | Sampson |
| 2016/0071392 | A1 | 3/2016 | Hankey et al. |
| 2016/0071393 | A1 | 3/2016 | Kaplan et al. |
| 2016/0093197 | A1 | 3/2016 | See et al. |
| 2016/0292850 | A1 | 10/2016 | Perez et al. |
| 2017/0066406 | A1 | 3/2017 | Ricci |
| 2017/0116845 | A1 | 4/2017 | See et al. |
| 2017/0150893 | A1 | 6/2017 | McCombie et al. |
| 2017/0193705 | A1 | 7/2017 | Mullins et al. |
| 2017/0347886 | A1 | 12/2017 | Tran |
| 2018/0184907 | A1 | 7/2018 | Tran |
| 2019/0038133 | A1 | 2/2019 | Tran |
| 2019/0113973 | A1 | 4/2019 | Coleman et al. |
| 2019/0192075 | A1 | 6/2019 | Kranz |
| 2020/0077892 | A1 | 3/2020 | Tran |
| 2020/0218350 | A1 | 7/2020 | Coleman et al. |
| 2021/0186329 | A1 | 6/2021 | Tran et al. |

OTHER PUBLICATIONS

Curone, et al. "An activity classifier based on heart rate and accelerometer data fusion." International Journal of Bioelectromagnetism 15.1 (2013): 7-12.

Sweeney, et al. "Identification of sleep apnea events using discrete wavelet transform of respiration, ecg and accelerometer signals." 2013 IEEE International Conference on Body Sensor Networks. IEEE, 2013.

Das, et al. "A Smart and Wearable Cardiac Healthcare System with Monitoring of Sudden Fall for Elderly and Post-Operative Patients." IOSR Journal of Computer Engineering 16.2 (2014): 126-133.

Kher, et al. An Investigation on Impact of Body Movement Activities on Wearable Ambulatory Electrocardiogram (A-ECG). Diss. Sardar Patel University.

Sun, X., et al. "Robust heart beat detection from photoplethysmography interlaced with motion artifacts based on empirical mode decomposition." Proceedings of 2012 IEEE-EMBS International Conference on Biomedical and Health Informatics. IEEE, 2012.

FIG. 1c
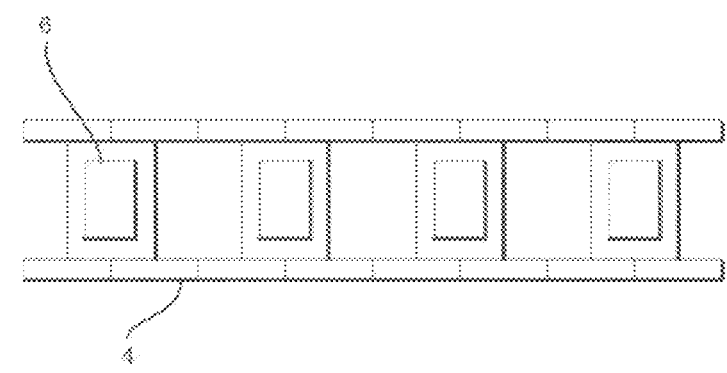
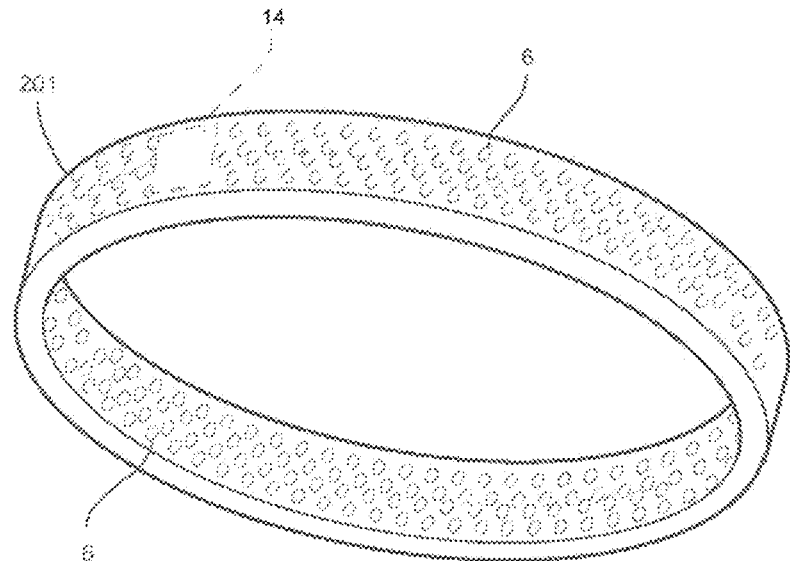
FIG. 2

10000

11000

| Produce apparatus | 11100 |
| Activate apparatus | 11200 |
| Compensate for movements | 11300 |
| Compare snapshots | 11400 |
| Transmit data | 11500 |
| Receive data | 11600 |

1

SYSTEM AND METHOD TO DETECT CHANGES IN HEALTH PARAMETERS AND ACTIVATE LIFESAVING MEASURES

CROSS-REFERENCE TO RELATED APPLICATIONS

This application is a continuation of U.S. application Ser. No. 16/687,344 filed Nov. 18, 2019, which is a continuation of U.S. application Ser. No. 14/748,230 filed Jun. 23, 2015, which claims priority to U.S. Provisional Application No. 62/015,844 filed Jun. 23, 2014, each of which is incorporated by reference in its entirety herein.

BACKGROUND

1. Field

Certain exemplary embodiments provide apparatuses, methods, processes, and/or systems related to detecting significant detrimental changes in health parameters, and facilitating help for the user. Systems, methods, processes and apparatuses, will most likely benefit people through the use of preferred embodiments that have widespread popular appeal, and thus can make the most substantial public health impact.

2. Discussion of Related Art

Certain exemplary embodiments address a question, "how can a patient, or a bystander, know when to activate the emergency response?" Those skilled in the art will recognize that it is common practice to use a resource rich device, such as a 12-lead, a 5-lead electrocardiogram (ECG, or also known as an EKG), or another device unrelated to the heart, which uses a significant amount of information to make a diagnosis. In the hands of a healthcare professional such as a doctor, or an EMT, a specific diagnosis can be made that pinpoints the problem. It can be extremely difficult to make a specific medical diagnosis without such analytical devices. However, a specific diagnosis is not necessary to acknowledge tempestuous changes in health that should cause alarm.

For the first time in history, multi-sensor capable devices (smart devices) are being popularized on millions of wrists (and other body parts) making implementation of lifesaving technology "fashionable," even if detecting a heart attack, or another health problem, is far from the primary reason someone may wear the device.

Embodiments that utilize watch form factor or another wearable biometric device, suffer from the reality that it takes a tremendous amount of computational ability and energy to make use of most sensors. Also, it is a problem that current inventions in the field do not fully conceptualize a system to deal with the difficulty of acquiring a resource poor signal that is so noisy; where the noise is often higher than the signal.

In addition, wearing such a device that integrates with a system may justify a change (increase/decrease) in insurance premiums, such as with life insurance, health insurance, or other insurances, based on the availability of more health parameters. In another example, insurance premiums may also justifiably be lowered as this apparatus and system lowers the probability of a catastrophic event from happening, and thereby will lower the cost to insurers.

SUMMARY

Certain exemplary embodiments address certain disadvantages mentioned above and consider additional aspects that have utility for the aforementioned application in the form of apparatuses, methods, processes, and systems.

Certain exemplary embodiments can utilize any wearable biometric device that a person could wear in a non-invasive fashion, preferably but not limited to the form of a commonly worn object. A biometric device can generally be considered any apparatus that gathers measurable inputs pertaining to an organism. Some examples of commonly worn objects are watches, eyeglasses, earphones, headphones, armbands, wristbands, ankle bands, jewelry (such as earrings, bracelets, necklaces, or rings), and/or other commercialized items. Ideally some people might not consider the apparatus to have any burden on their lives. The intent of such a device is to so seamlessly fit into the fabric of everyday lives, that this device could possibly be an add-on to another device and need not necessarily be a device independently designed for detecting health related parameters.

Certain exemplary embodiments can be adapted to detect and alert individuals of significant detrimental changes to any health related parameters while minimally impacting a user's daily life. A preferred embodiment of the apparatus detects significant detrimental changes in cardiac and/or neurologic activity, as well as but not limited to changes in heartbeat, blood pressure, heart rate, cardiac electrical signature, neurologic electrical signature, pulse transit time or any other signal generated directly or indirectly by the user's heart or brain, and/or other biometric outputs; in order to give a patient and/or surrounding people advanced warning of a health related issue; and/or to activate the emergency medical system (EMS); and thereby efficiently transfer himself or herself to the appropriate healthcare professional. Alternatively, the apparatus can also warn a healthcare professional directly, such as but not limited to a physician, a government service, or non-government service, that can notify the user of the significant detrimental changes in their cardiac and/or neurological activity, and encourage the user to seek medical attention. Such an apparatus can also seek the help of a healthcare professional if the patient is unable to do so.

An exemplary biometric apparatus can use any means of detection such as, but not limited to, electric, magnetic, optical, acoustic, pneumatic, thermal, nuclear, mechanical, hydraulic, and/or vacuum, etc. Certain exemplary embodiments can detect a myocardial infarction (MI), also known as a heart attack, but could also relate to other presentations, conditions, and diseases such as sudden cardiac death (SCD), stroke, seizure, hypertension, hypotension, arrhythmia, vascular aneurysm, congestive heart failure, valvular heart disease, cardiac muscle disease, tumors, Alzheimer's disease, dementia, psychosis, sleep disorders, attention-deficit/hyperactivity disorder (ADHD), coma, head injuries, infections, and/or death, and many others not explicitly specified. Certain exemplary embodiments are not limited to emergency situations, but can also be used in non-emergent situations, such as routine check-ups and yearly physicals, as well as in other situations. Those skilled in the art will understand that changes in cardiac and/or neurologic activity can be indicative of other medical problems not directly stemming from the heart or brain, and can be used as a valuable diagnostic indicator for many reasons.

Electrocardiography (ECG) and electroencephalography (EEG) are considered by some to be the gold standard techniques to monitor a heart and brain respectively, but there are also other useful technologies that make use of pulse oximetry, laser Doppler flowmetry (LDF), ultrasound, piezoelectricity, capacitance, temperature, radioactivity, and/or other non-invasive diagnostic technologies. ECG and EEG sensors have substantial utility in a wearable biometric device for the purpose of assessing changes in a heart or brain due to the quantifiable nature of electric properties. However, the pairing of an ECG sensor, or an alternate sensor, with another non-invasive sensor can be useful, but is not required, for a variety of reasons. One reason is to rule out conditions such as pulse-less electrical activity (PEA), where it is possible to have an unremarkable ECG, but to have a heart that does not mechanically function—obviously a life threatening issue to a patient. Another reason is that it is possible to greatly enhance the accuracy of the preferred embodiment by synergistically incorporating data from two or more sensors. To detect a user's changes in heartbeat, blood pressure, heart rate, cardiac electrical signature, neuronal electrical signature, pulse transit time, or any other signal generated directly or indirectly by the user's heart or brain, or other biometric outputs, the biometric apparatus can include one or more embedded sensors; for example, an ECG sensor and/or a laser Doppler flowmeter.

The ECG and/or EEG sensor(s) of an exemplary apparatus can comprise at least two electrodes, as both modalities operate on the principle of voltage difference. To maximize voltage difference for an ECG on the wrist, one electrode could be placed within the case back of the watch, and another could be placed on the band on the substantially opposite side. To maximize voltage difference for an EEG contained within eyeglasses, one electrode could be placed on each side of a user's head by the ear. Those skilled in the art will recognize that there are a variety of placements that the electrodes can be located to achieve similar results, especially when considering the ideal proximity of a complementary sensor that can be similarly placed within the case back of the watch or band, the frame of eyeglasses, or other locations. It should be noted that relatively close placement of electrodes, such as points around one wrist, can result in noise and difficulty in obtaining a signal.

Therefore, it is advantageous, but not required, to incorporate multiple types of sensors in order to assist a lifesaving algorithm by creating more data points, thus mitigating ECG data noise from the wrist or another distant point from the heart. By taking an ECG in this manner, many times it has been found that the noise is more pronounced than the true signal, thus creating a significant obstacle. The same concepts can be applied to a noisy EEG with only two electrodes providing data. In one embodiment where an ECG and a laser Doppler flowmeter are used, the laser Doppler flowmeter can detect the beats of the heart, and create tight ranges for signal processing to search for the heart's normally periodic electrical signals within the repository of collected ECG signals from the user. For example, it is much easier to look for a P wave, QRS complex, or T wave, when it exists within certain finite ranges. Moreover, it is far easier to find one of the most pronounced signals—the QRS complex—if a determination can be made of the limits of the ECG signal (the voltage difference and time), and determine where the periodicity of the ECG data lies so signal processing knows how and where to search. Having a repository of collected signals from the user can be useful in cleaning up signals, as it can provide more data and improve the algorithmic capability for detecting significant detrimental cardiac and/or neurological changes in a person.

It can also be advantageous, but not required, to create a redundant number of sensors because biometric devices disguised as commercialized accessories, such as watches, are worn in a variety of ways. An example of an immediate issue is the fact that people wear their watches on different wrists depending on their preference, or their handedness. In some cases, it may be necessary to reverse the directionality of the data from the sensor to capture the correct signal, or to use different sensors to capture the correct data if one is not adequately contacting the individual. In the embodiment of a watch, it may be important for the watch's interface to ask the user what wrist they are wearing the device on, or for the watch to make this determination automatically. Even preferences such as the tightness of the watch can affect performance, but that issue can be mitigated by having sensors at a variety of high probability contact points, such as the case back of the watch, the left and right interior edges of the watch band, the clasp, the part of the band directly opposite the watch's case back, and other components of the watch. Those skilled in the art can envision how the idea of redundancy broadly applies exemplary embodiments.

A key issue can be the clarity of the ECG signal that can be achieved when electrodes are placed in such close proximity to each other, especially when they are distant from the heart. In such embodiments, the use of highly conductive sensors, high fidelity analogue to digital (A/D) converters, signal processing, algorithmic analysis, and primary processors and power supplies make the detection of a noisy ECG possible. Other embodiments can further clarify the signal or provide other useful information, which can include wearable devices in two or more places on the body in wireless or wired communication with each other; for example, a watch with eyeglasses, or a watch with a wristband on the other arm.

An embodiment of the system that controls the process pertaining to the apparatus is the use of sensors, amplification (for example, an operation amplifier and/or a lock-in amplifier can be used), simple filtration (low pass, high pass, band-pass, and notch filters may be used), analog to digital converter, minimal processing only sufficient to govern the aforementioned process or transmit to another apparatus or primary processor, a wireless transmitter or wired connectivity to the primary processor, and a power supply large enough to power these items are housed within the main biometric apparatus. The main processing, algorithmic calculations, and main power source to supply the bulk of these lifesaving activities will take place on the primary processor, which can be a portable smart device, such as a cellular phone, a "cloud," or remote computers/servers. In an exemplary embodiment, the biometric apparatus itself can either be responsible for directing a communication to a call station, or the cloud or a remote processing device (such as a smartphone) can be responsible.

Those skilled in the art will understand the complexity of performing mathematical calculations, and filtration, as well as running an algorithm in a resource poor environment such as a wearable apparatus (for example: a watch), which necessitates primary processing on a more powerful (both computationally, and energetically) device such as a smartphone, or a networked cloud application or Software As A Service (SaaS) application. Primary processing can be used to determine if someone is having significant changes in health related parameters by utilizing or performing any of the following, but not limited to: waveform analysis, filtration (band pass filtration, finite/infinite response filters, adaptive filters, Gabor filters, and/or other filters), decimation, Hilbert transformation, deconvolution, wavelet denoising, time series analysis, empirical mode decomposition, confidence intervals, normalization/standardization, significance testing, stochastic modeling, machine learning (deep learning, artificial neural networks, and other types of learning), iterative reconstruction, fast-Fourier transform (FFT), compressed sensing, expectation-maximization algorithm, averaging, probability distributions, standard deviation, slope, bootstrapping, and/or pattern recognition, etc. Other mathematical or statistical tools can be used to achieve the same goal as certain embodiments without departing from the spirit and scope thereof.

A wearable biometric device has several constraints that might limit its capability in detecting a significant detrimental change in health parameters and activating EMS: size, processing power, and/o electrical capacity, etc. Utilizing a coupled smartphone or SaaS/cloud solution as part of the system can address such constraints.

Such embodiments might comprise a dependency between the wearable biometric device and the secondary device with superior computational power, energy reserves and signaling capability for EMS activation. Instead of simply just buying a wearable biometric apparatus in the form of a watch, a user may also utilize a tethered smartphone or the like. In another embodiment, a user of the wearable biometric device could subscribe to an online cloud service that provides additional processing and EMS activation (without the use of a smartphone), as long as the wearable device is in communication with the cloud service (for example through Wi-Fi and/or any other form of transmission). From an economic standpoint, such embodiments can have an advantage as they tie consumers into a wider ecosystem/service/platform of products and can boost revenues. Those skilled in the art understand that are a multitude of ways a biometric device can be in communication with other devices or services to achieve the aforementioned purposes.

The signal on the biometric device can communicate via wired or wireless communication with any supporting device via any practical means necessary, which could come in the form of Bluetooth, Wi-Fi, radio, ZigBee radio, a cellular network, or any other form of electromagnetic radiation. As with all biometric data, it is important to safeguard the information due to the personal information it carries. In this embodiment, that can be accomplished by the storage of data on a secure microprocessor that is architecturally separate from any other processor, and the data can be secured with any feasible level of encryption. This is especially important for when information is being broadcasted wirelessly.

Almost as important as making a correct determination of an imminent health issue is the rejection of false alarms. In order for both civilians and healthcare professionals to trust the analysis of this embodiment, it is important that the accuracy is exceedingly high. In order to achieve this result, not only is it necessary to have high signal-to-noise discrimination measures, but also it can be important to have prohibiting factors. An example of a prohibitive factor could be a sensor, possibly through the use of a primary processor, that registers magnetically, electrically, mechanically, temperately, makes use of biometric outputs, and/or uses any other means to detect if the watch is being worn. For instance, a magnet that registers that two sides of a watch clasp are engaged and indicates the watch is being worn could guard against the embodiment from identifying a change in health parameters symbolic of a cardiac arrest when an individual is simply not wearing the apparatus. A pulse oximeter, laser Doppler flowmeter, and/or another biometric sensor could be used to detect if the device is contacting a body in the first place. Some prohibitive factors should also be user controlled, such as a way for a user to permanently or temporarily turn off the EMS activation feature for any number of reasons including but not limited to drug use, or a desire for additional privacy.

False alarms can also be lessened in number by taking into account the confidence the algorithm has in determining changes in biometric activity. One simple mechanism to adjust the weighting of different parts of the algorithm can be to take into account the user's age, race, height, weight, allergies, prescriptions, immunizations, past medical history (for example, pre-existing conditions, if the patient had surgery, a stent placed, or any other history), family history, and/or prior sensor usage patterns, etc. Examples can include: it is many times more likely a heart attack will occur in a 70 year old than a 20 year old, or in someone who has an irregular heartbeat.

Once a determination of high confidence is made that a user is having significant detrimental changes in a health parameter (an event), as a result of primary processing outside the sensing apparatus (for example in the smartphone or cloud service), an alert can be generated to thereby alert the individual, a caregiver, or the immediate surroundings of the event, and give them a short period of time (30 seconds for example) to validate, or disregard the concern. The alert can come in any form, including but not limited to an audible alarm, a visual queue like a strobe light or red/blue flasher, vibration, etc. The alert can also initiate a text message, or phone call alert to appropriate parties through a smartphone or a service. A simulation mode can be exercised through initial setup training to practice this scenario for the individual or caregiver. With either an affirmative confirmation or the lack of a response, certain exemplary embodiments can initiate communication with a call station with some combination of the users name, gender, GPS coordinates and location, permanent address (or address they spend most time at), meta-data, and/or other parameters discussed in "information input" within the detailed description of the patent that could either allow a call station to triage a patient, or it could immediately activate EMS in a time-saving manner that would not have otherwise been possible without a biometric detecting apparatus in communication with the proposed system. When an alert is issued, the user or call station can initiate a two-way or one-way communication in the form of an audio and/or video connection through the apparatus to check on the user, more adequately preparing EMS for the situation at hand.

If a low, but a still significant confidence interval were calculated, certain exemplary embodiments can alert the user, or other parties of its findings, and ask the user what should be done. If the user declines the alert, nothing would be done. However, if either the patient requests help, or if no action is taken by the user within a short period of time, a communication would be initiated to a call station; ideally (but not imperative), the apparatus and system can autonomously use the algorithm to determine an emergency situation, and activate lifesaving measures through EMS activation. However, in other embodiments, a government or non-government call station or even a healthcare professional could be tasked with reviewing possibly relevant changes in health related parameters with or without the algorithm. Revenue to pay for costs can be either recovered from any combination of: the price of the system, a service charge from a data plan, a service subscription charge, an emergency tax such as enhanced 911 (E911), and/or insurance premiums, etc.

Calibration can occur simply and with minimal action from the user, or a more advanced-calibration can occur with user cooperation. While not required, having reliable baseline biometric data gathered in a conventional way from two very different parts of the body, such as a signal from the wrist of one hand and the wrist of another hand, can increase the capability of exemplary algorithms to differentiate a signal from noise in a resource poor environment and boost the algorithms confidence in its determination of changes in health related parameters requiring EMS activation. Although not required, there could be an advanced-calibration where the user wears the biometric apparatus on one extension of their body, and touches the device with their opposing hand, thus contacting a sensor that completes a circuit around their body. Calibration can occur much like how there is an initial training phase in most fingerprint scanners. Consequently, certain exemplary embodiments can utilize baseline data obtained from another apparatus to aid in calibration, such as a phone, and/or any other paired or unpaired biometric apparatus, including a resource rich device.

Multiple users can use certain exemplary biometric apparatuses; biometric readings from such can be logged per user if there are multiple users for the apparatus. Alternatively, a second wearable apparatus, such as an RFID tag, badge, implant, or another close-proximity identifiable signature can be used to determine the active user. This will insure that the calibration and detection phases do not mislead the lifesaving algorithm if multiple people use the apparatus and system.

Disclaimers may need to be provided to user during use, and during the initial opt-in confirmation, especially if used as a "medical device," similar to a prescription or a durable medical equipment only being useable by the patient. A preferred embodiment is to use the sensor apparatus and alerting/EMS activation system as a utility to more proactively get help, not to make a diagnosis.

Various exemplary embodiments—apparatuses, methods, and systems—are illustrated in (but not solely limited to) the drawings. The following descriptions of each figure give more explanations about the disclosed apparatuses, methods and systems. Note that the figures are for the purpose of illustration. Actual physical implementation may take a plethora of different forms. All changes and substitutions within the spirit and technical scope of the disclosed embodiments are indeed encompassed in the present application. These and other objects and advantages of the disclosed embodiments will no doubt become obvious to those of ordinary skill in the art.

BRIEF DESCRIPTION OF THE DRAWINGS

A wide variety of potential, practical, and useful embodiments will be more readily understood through the following detailed description of certain exemplary embodiments, with reference to the accompanying exemplary drawings in which:

FIG. 1c shows a design for a watch band with links that embodies at least one of the following biometric sensors: ECG, pulse oximeter, laser Doppler flowmeter, or other biometric sensors;

FIG. 2 shows an apparatus in the form of an armband that embodies at least one of the following biometric sensors:

Figures 3A, 3B:
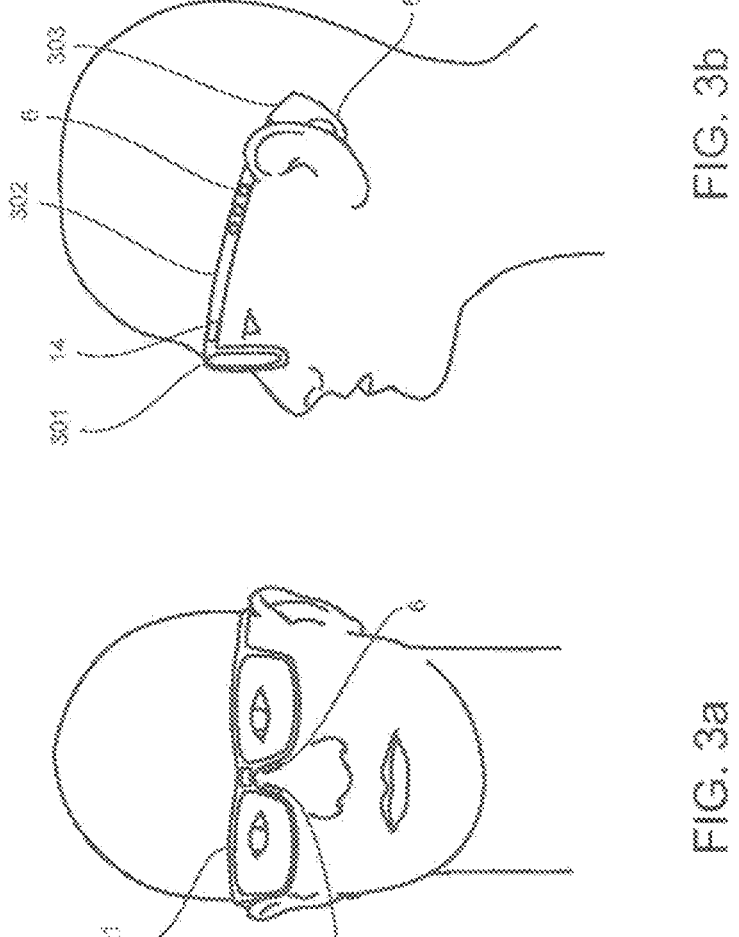
Figure 4:
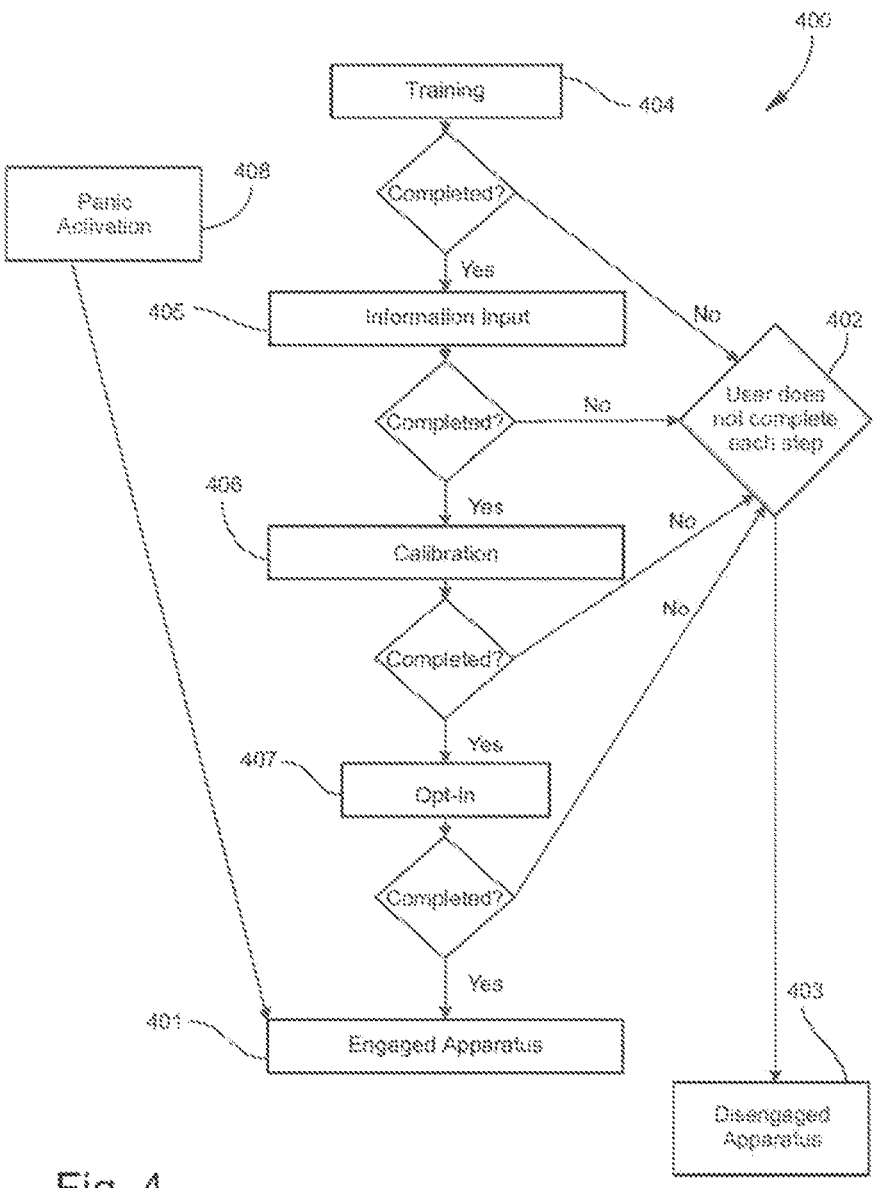
Figure 5A:
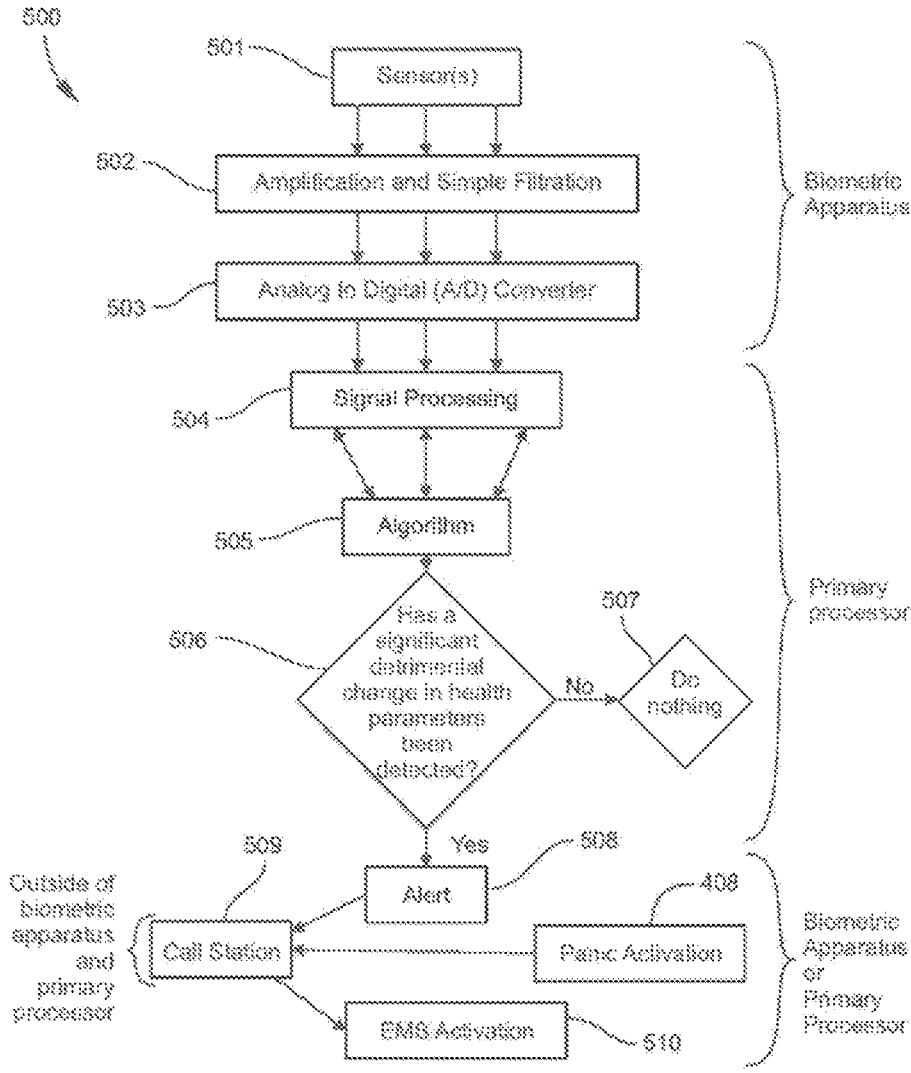
Figure 5B:
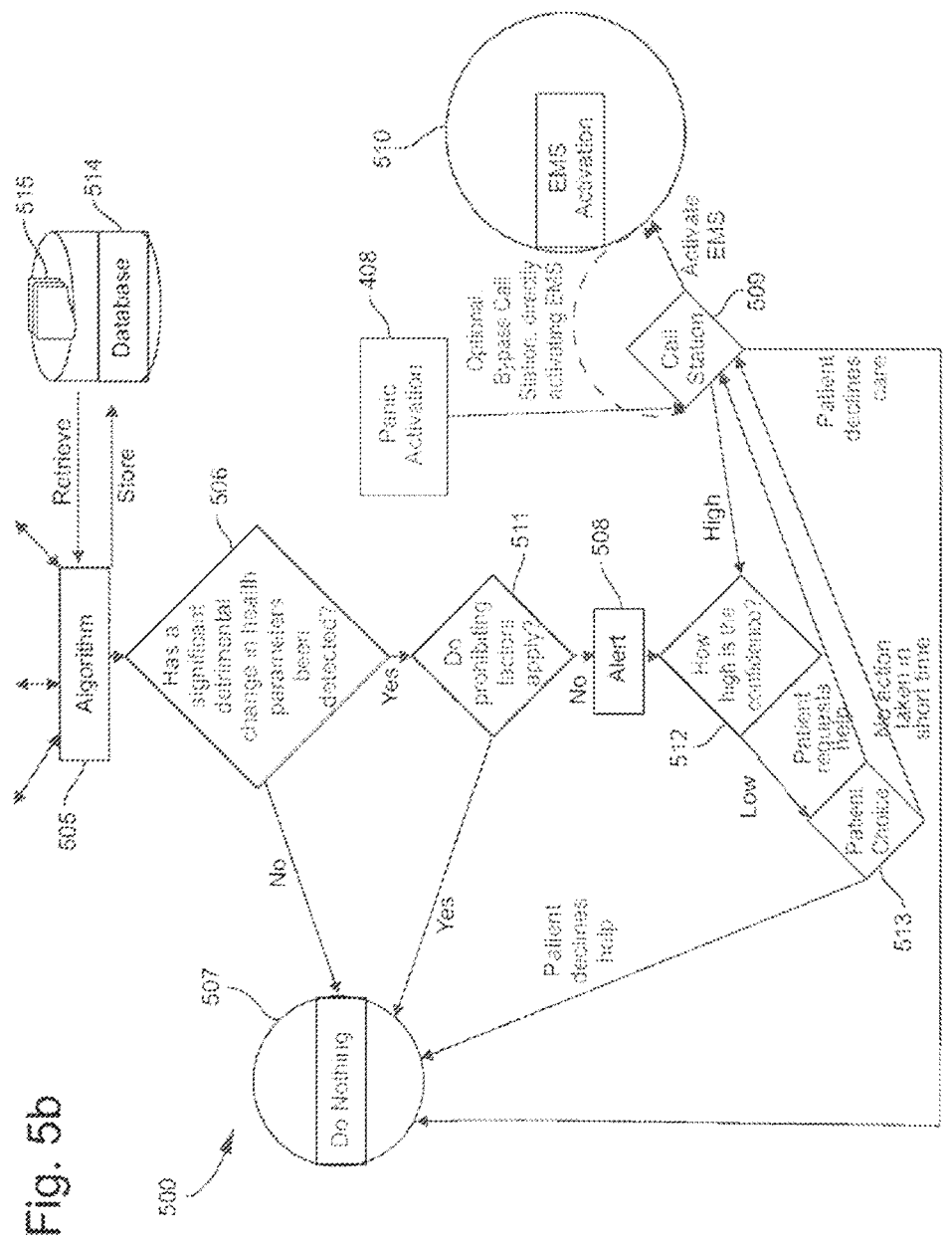
Figure 6:
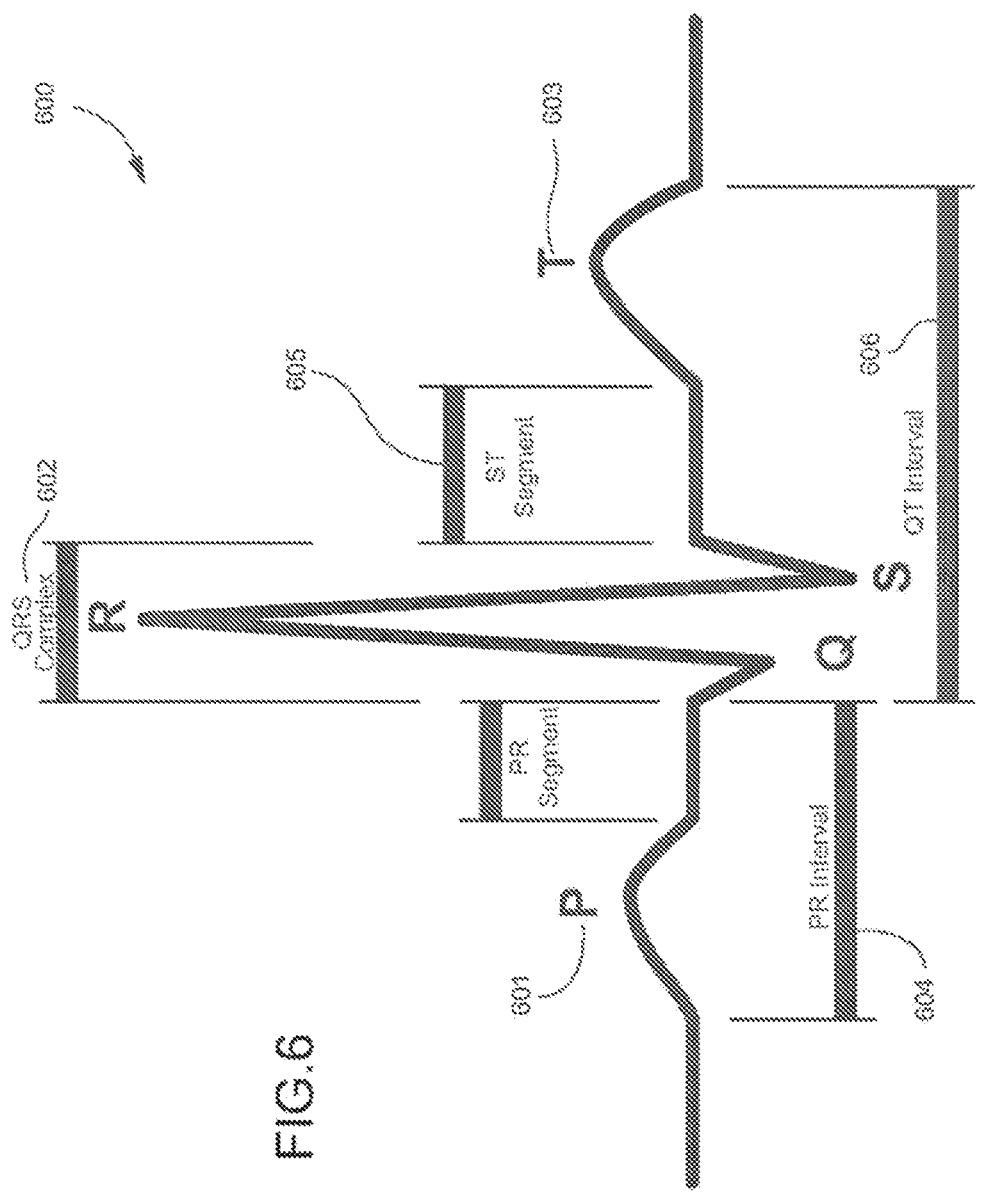
Figure 7:
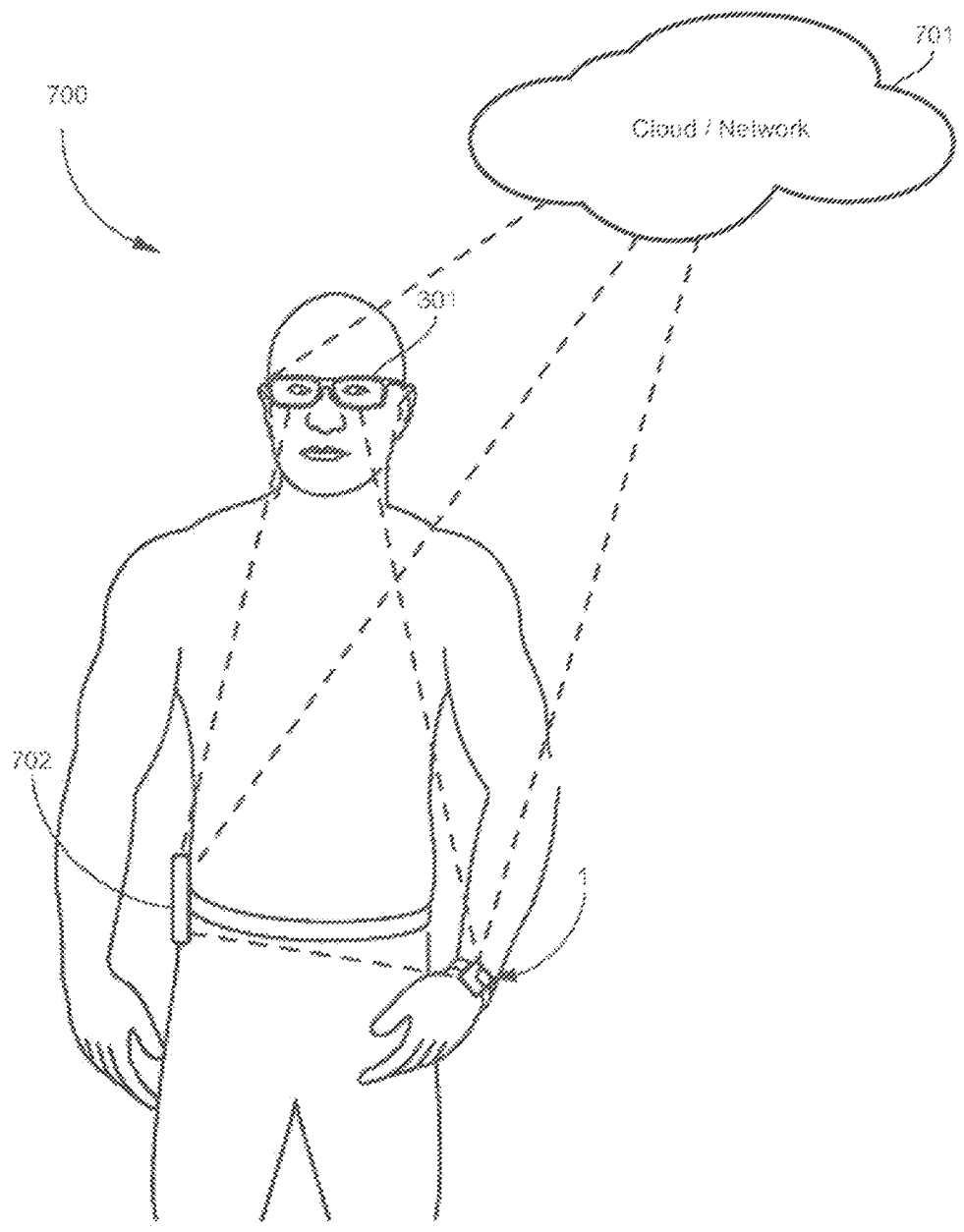
Figure 8:
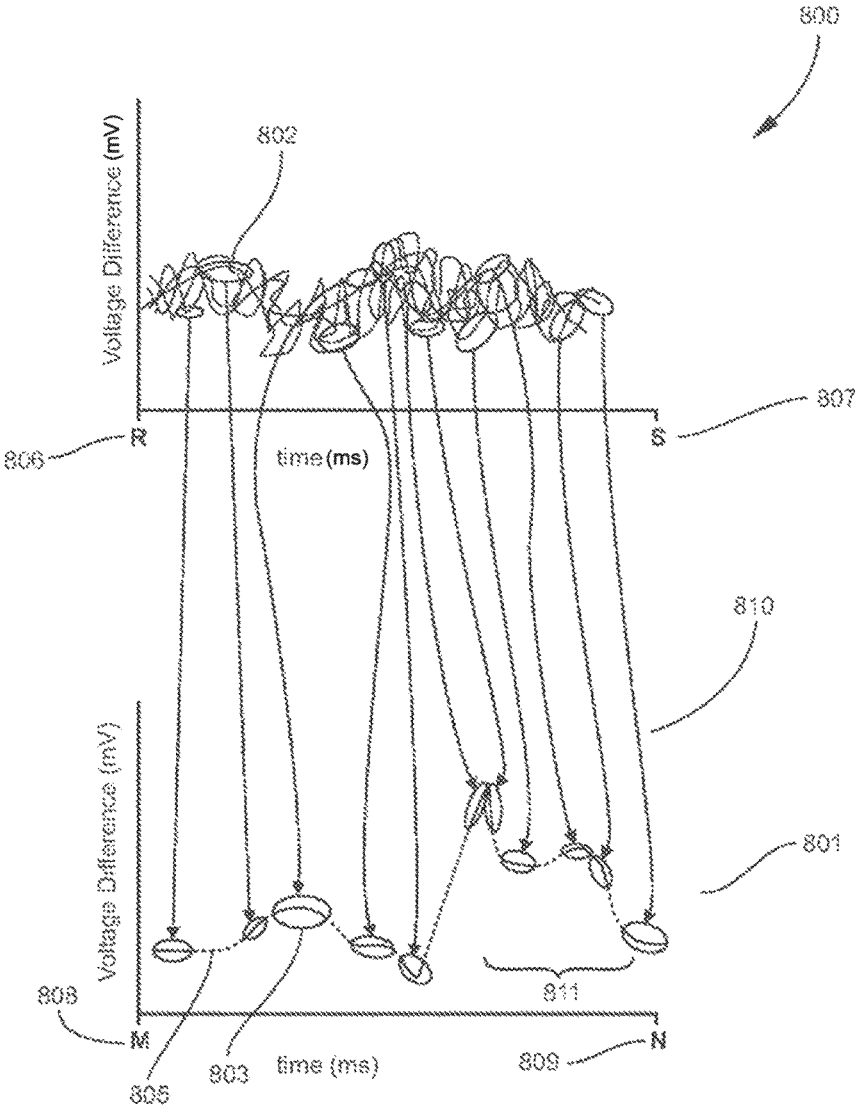
Figure 9:
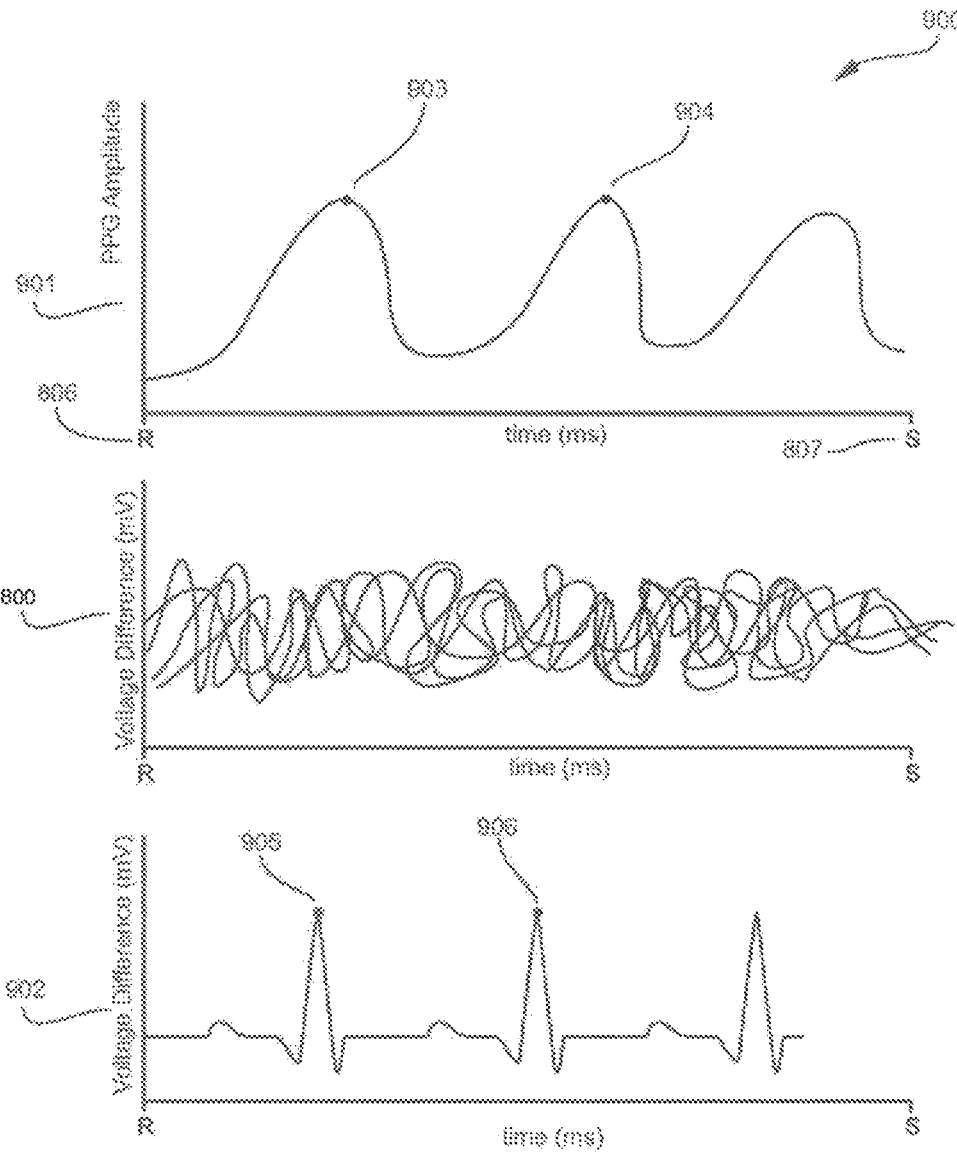
Figure 10:
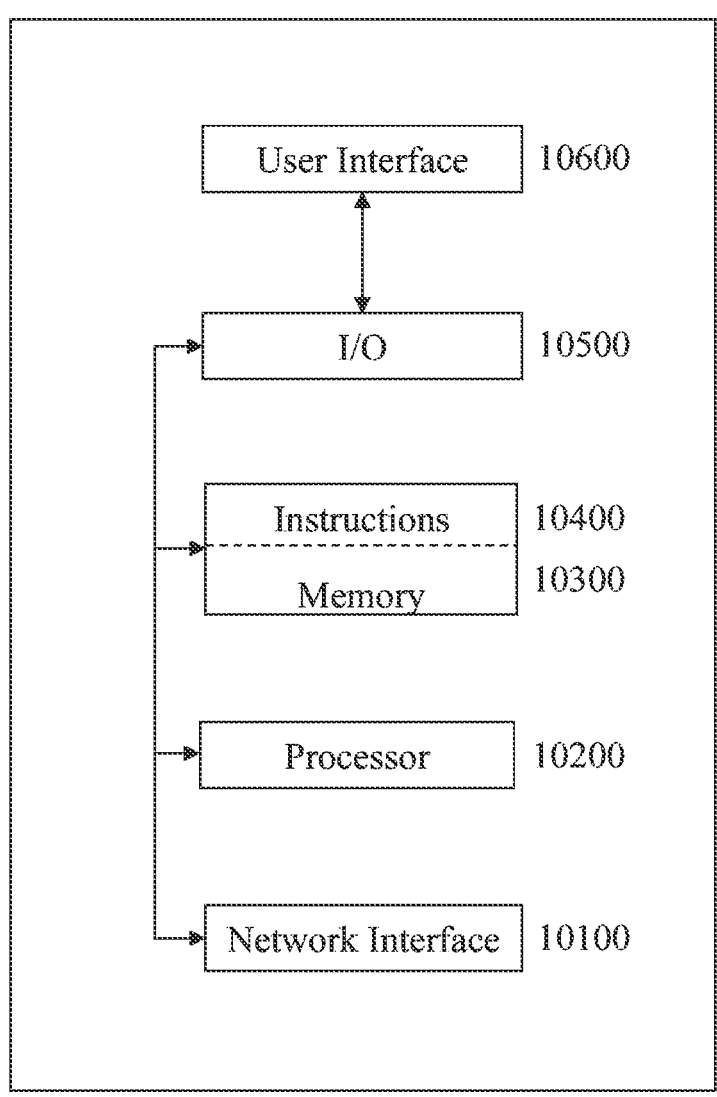
Figure 11:
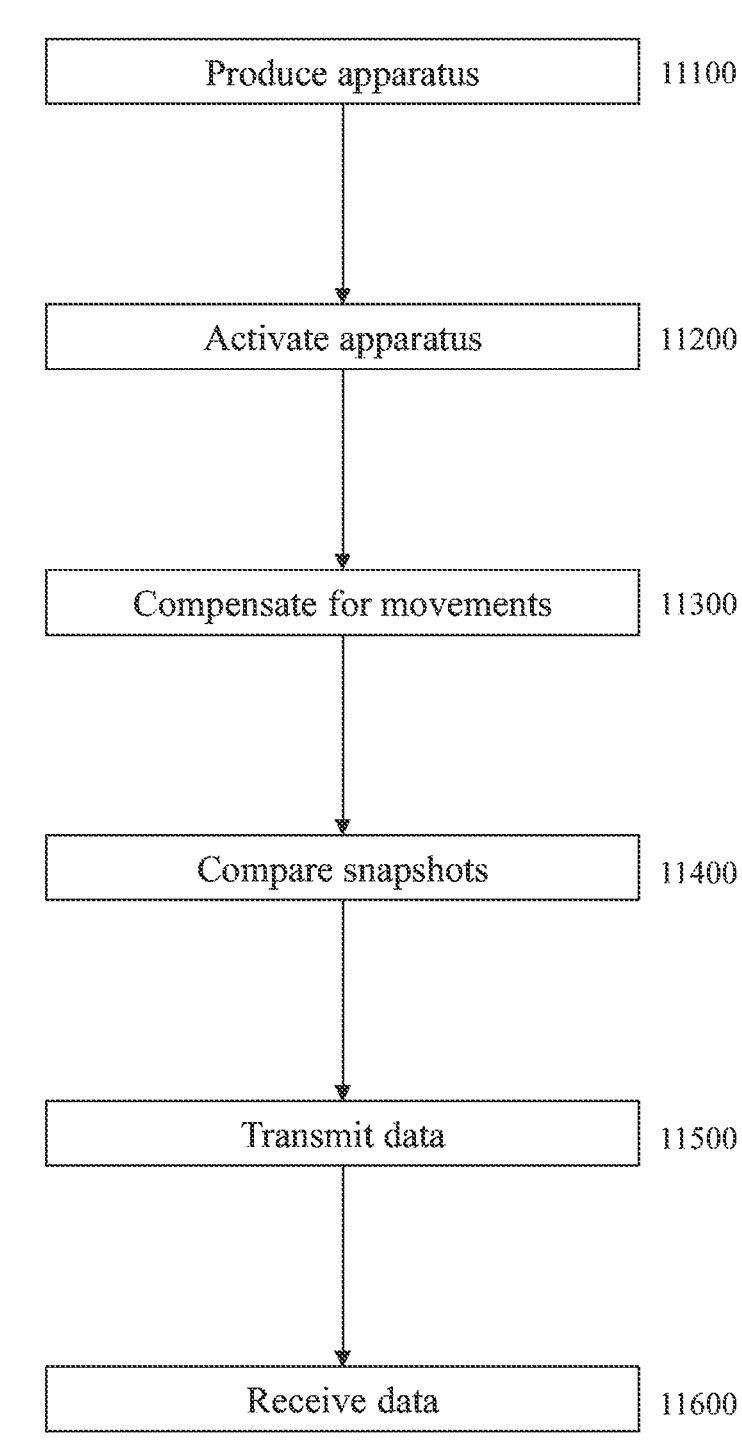

ECG, pulse oximeter, laser Doppler flowmeter, or other biometric sensors, and also depicts a way to increase the clarity of the signal;

FIG. 3a show an apparatus in the form of eyeglasses that embodies at least one of the following biometric sensors: ECG, pulse oximeter, laser Doppler flowmeter, or other biometric sensors;

FIG. 3b shows a side view of an apparatus in the form of eyeglasses that embodies at least one of the following biometric sensors: ECG, pulse oximeter, laser Doppler flowmeter, or other biometric sensors;

FIG. 4 shows a method for steps a user may complete in order to have an engaged apparatus, and a method for panic activation;

FIG. 5a shows a flowchart of the system that illustrates what, how, and where elements of the system function. It also details processes that connect the system;

FIG. 5b shows a magnification, extension, and elaboration of the system depicted in FIG. 5a;

FIG. 6 shows a representative ECG of a healthy heartbeat;

FIG. 7 shows a schematic of how apparatuses can be in communication with primary processors and integrate into the system;

FIG. 8 demonstrates two signal processing methods in detail involving at least one biometric sensor, adaptable to different types of sensors;

FIG. 9 demonstrates a signal processing method in detail involving at least two biometric sensors;

FIG. 10 is a block diagram of an exemplary embodiment of an information device 10000; and FIG. 11 is a flowchart of an exemplary embodiment of a method 11000.

DETAILED DESCRIPTION

Figures 1A, 1B:
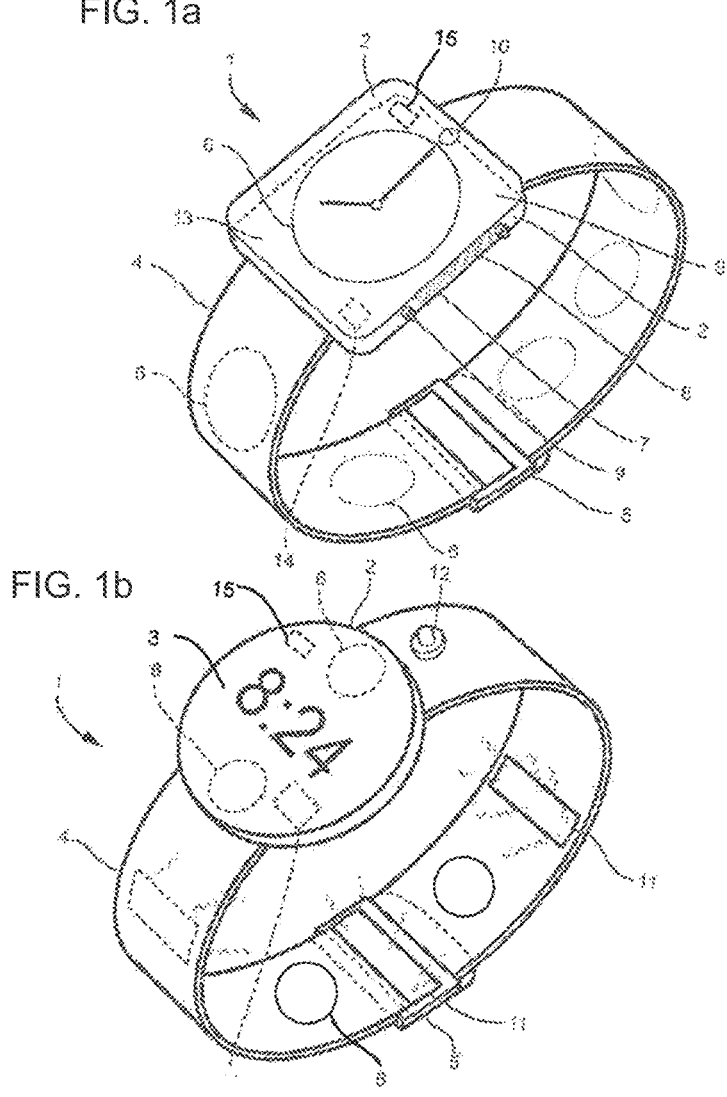
FIG. 1a shows an apparatus in the form of a smartwatch that embodies at least one of the following biometric sensors: ECG, pulse oximeter, laser Doppler flowmeter, or other biometric sensors.
FIG. 1b shows an apparatus in the form of a different design of a smartwatch that embodies at least two of the following different biometric sensors: ECG, pulse oximeter, laser Doppler flowmeter, or other biometric sensors.

Referring to FIG. 1a, there is shown a wearable biometric apparatus 1, in the form factor of a watch that functions as part of the system of a preferred embodiment. The biometric device illustrated is composed of case 2 (a casual observer would call this the rim of the watch), case back 13, display 3 (either analog or digital, and potentially a touch screen), band 4, power supply 15, and clasp 5, which are all parts of exemplary wristwatches. The biometric apparatus can comprise at least one or more biometric sensor(s) 6, which may be an ECG sensing electrode, or any other technology mentioned within this application, or a similar technology (note: dotted lines in the figures represent placement on planes not visible from the observer's point-of-view). All sensors on the apparatus, including sensor(s) 6, can be designed in such a way as to improve the utility of the health related data and the comfort for the user. Within case 2 there exists an electronic area 14 that can comprise a minimal processor sufficient to govern the aforementioned process and/or transmit to another apparatus or primary processor, a wireless transmitter and/or wired connectivity to the primary processor, and a power supply large enough to power these items, for the purpose of handling input signals from the various biometric sensors, such as sensor(s) 6, and any other systemic reasons. Multiple copies of sensors (even the same type of sensor) can assist in obtaining a sufficiently clear signal, which is represented by multiple placements of sensor(s) 6. Sensor(s) 6 can take any location, size, shape, texture, material (alloy, impregnated material, and/or coating, etc.), etc., that meets the goals of preferred embodiments. In addition to sensor(s) 6 adding an additional component to apparatus 1, parts of the apparatus themselves can be made into a sensor. For example, clasp 5 in its entirety, or through a coating that only contacts the users arm, can be a sensor, such as an ECG sensing electrode. If sensor(s) 6 is a conductive lead for an ECG, it is recommended but not required to be made of a highly conductive material, such as titanium nitride (TiN), titanium carbide (TiC), or titanium carbo-nitride (TiCN), which can be plated using known chemical or physical vapor deposition or other techniques. Another highly conductive material that can be utilized is silver-silver chloride (Ag/AgCl). While Ag/AgCl is possible to use in this embodiment, it might not be as desirable due to the residue it leaves behind and the need to constantly replace the coating, which can be somewhat problematic. Band 4 can be made out of any suitable material, for example leather or stainless steel, but should either be electrically insulated, or have a relatively high electrical resistance. Sensors that detect changes in health related parameters should be protected from water with a hydrophobic coating or another waterproofing measure, unless the sensor is intended to measure fluids, such as sweat.

A user wanting to operate apparatus 1 will open clasp 5, comfortably put the apparatus on their body, and close clasp 5, which should allow sensor(s) 6 and/or sensor(s) 11 (FIG. 1*b*), which may be part of the clasp itself, to contact the user's body. If sensor(s) 6 comprises an ECG sensor, it should contact the user in at least two locations, preferably as far apart as possible, such as within or on case back 13, and on the interior edge facing the user of clasp 5. Case 2 is shown with both solid and dashed lines to illustrate dimensionality. Input and output functions of apparatus 1 can take place via display 3 (which can be a capacitive touch screen), by microphone 7, video camera 10, and/or any number of other means, including but not limited to action button 9. Display 3 can also render data feedback related to health parameters, or non-medical functions of the apparatus, such as text messages, or the time. Apparatus 1 can utilize speaker 8 to obtain audio output, in addition to feedback on display 3, or another device. If a two-way or one-way communication is warranted, video camera 10, microphone 7, and/or speaker 8 can be utilized, which can be useful in the event of an emergency.

In order to initiate calibration more accurately than what the system may be capable of autonomously conducting, calibration can be conducted while wearing the apparatus by gripping case 2 on opposite sides (with the opposing hand), which can be another form of biometric sensor 6, or a user can press their opposing finger against any one of the appropriate sensor(s) 6.

Referring to FIG. 1*b*, there is another example of a wearable biometric apparatus 1, in the form of a watch, which can function as part of the system of a preferred embodiment. FIG. 1*b* demonstrates the possibility of multiple types of sensors working synergistically to achieve the aims of this application by combining sensor(s) 6, which can be an ECG electrode, and sensor(s) 11 (shown with hypothetical sensing waves coming out of sensors), which could be one or more of different types of biometric sensors, such as a laser Doppler flowmeter or another type of sensor. Sensor(s) 11 can take any location, size, shape, texture, material (alloy, impregnated material, and/or coating, etc.), etc. that meets the goals of the preferred embodiment. FIG. 1*b* shows two or more sensor(s) 6 on the underside of case 2 at substantially opposite sides of each other, which contrasts one possibly large sensor(s) 6 in FIG. 1*a*, due to the possibility of solely acquiring a signal in that fashion with those two contact points. The apparatus can also be controlled (or calibrated) by action button/sensor 12, (which could also double as a biometric sensor or can be pushed), or another type of sensor(s) 6 (such as a capacitive sensor) on the exterior side of band 4, and/or display 3. If action button/sensor 12 is also a sensor, it can be used to calibrate the system more accurately than what the system may be capable of autonomously conducting. While wearing the apparatus, a user can press their finger on action button/ sensor 12 from their opposing hand when prompted in a way described much like in FIG. 1*a*. The embodiment illustrated in FIG. 1*b* comprises an electronic area 14 and a power supply 15.

Referring to FIG. 1*c*, there is an example of a variation of how a biometric sensor can be incorporated into the band 4 of a watch, or some other apparatus with a band or band links. On some, or all of the links contain upon or within them biometric sensor(s) 6, comprised of a highly conductive material such as TiN, which are in contact with the user of the apparatus. Such an embodiment can improve the sensitivity of the sensor and the comfort for a user.

Certain exemplary embodiments provide a system, which can comprise an apparatus wearable by a user (e.g., wearable biometric apparatus 1 of FIG. 1*a*). In certain exemplary embodiments, the system can be constructed to: analyze and compare a plurality of snapshots with each other; and/or compare at least one of the plurality of snapshots to a standard snapshot.

In certain exemplary embodiments, the apparatus is worn on a wrist of the user (e.g., wearable biometric apparatus 1 of FIG. 1*a*). In other embodiments, the apparatus can partially surround a head of the user (e.g., wearable biometric apparatus 301 of FIGS. 3*a* and 3*b*). The apparatus can comprise one or more of:

a biometric sensor (e.g., biometric sensor(s) 6 of FIG. 1*a*) constructed to generate signals based upon measurements of the user;

a plurality of biometric sensors (e.g., biometric sensor(s) 6 of FIG. 1*a*);

a user interface (e.g., display 3 of FIG. 1*a*) that causes the apparatus to capture a reading from the biometric sensor;

a processor (e.g., a processor comprised by electronic area 14 of FIG. 1*a*) constructed to provide information to an entity;

a power supply constructed provide energy to the apparatus, the power supply comprising a charging mechanism;

a signal filter constructed to average signals from the biometric sensor;

a power supply constructed provide energy to the apparatus, the power supply can comprise a charging mechanism;

a signal filter constructed to average signals from the biometric sensor;

a medical device mode and a non-medical device mode; and/or a wireless transmitter (e.g., a wireless transmitter comprised by electronic area 14 of FIG. 1*a*), the wireless transmitter can be constructed to wirelessly transmit the signals to an information device via a network, the information device can be constructed to:

determine a confidence level associated with the signals;

determine a significant detrimental change in the user via an algorithm based upon the signals and the confidence level, the significant detrimental change determined via decision tree;

relay information concerning the significant detrimental change to the apparatus.

receive information concerning an established confidence interval for the averaged signals; and/or receive information concerning predicted timing of a signal from the biometric sensor based upon a pulse oximeter obtained via at least one of:

the pulse oximeter of the user bounded by a QRS complex; and/or the QRS complex can be obtained via by pulse waves bounded by the pulse oximeter; etc.

Depending on a recommended action determined by a decision tree, the apparatus and/or the information device can either automatically notify an emergency medical system concerning activation of the apparatus or prompt the user to activate the apparatus with the emergency medical system. Responsive to user signals from the user, the apparatus can be constructed to calibrate the biometric sensor based upon demographical and medical information received from the user. The calibration can comprise a determination of differences between a signal of the biometric sensor and a standard.

In certain exemplary embodiments, the biometric sensor can be:

an electrocardiogram sensor that can be constructed to couple to the user in at least two locations and/or comprise at least one of a titanium nitride lead, a titanium carbide lead, and/or a carbo-nitride lead;

one of a plurality of electrocardiogram sensors that substantially surround an arm of the user;

a heart rate monitor;

a laser Doppler flowmeter;

a capacitive sensor that comprises two electrodes constructed to be mounted on substantially opposite sides of a body part of the user;

selectively calibrated based upon information from one or more biometric sensors either individually or as a group;

calibrated based upon sensor signals from a plurality of locations of a body of the user; and/or a sensor that comprises a hydrophobic coating; etc.

In certain exemplary embodiments, the algorithm can analyze a snapshot of the signals and/or utilizes photoplethysmogram sensor data. The algorithm can be constructed to:

determine that the significant detrimental change in health parameters has occurred in the user based upon changes in a QRS complex;

determine that a stroke has occurred based upon ST depression; and/or be automatically changed based upon a selective count of biometric sensors in the system; etc.

The apparatus can be constructed to:

automatically notify the user of the significant detrimental change;

prompt the user to submit past, family, and social history information via a user interface of the apparatus or the processor;

receive past, family, and social history information;

automatically communicate past, family, and social history of the user to the emergency medical system;

create a calibration profile for health parameters of the user based upon information from the biometric sensor, the calibration profile constructed for use in calibrating the biometric sensor;

allow the user to cancel an information transmission to the emergency medical system;

automatically prompt the user for information responsive to information from the biometric sensor;

receive profile information for a predetermined activity from the user;

determine a velocity of the user;

be activated on the emergency medical system and transmit medical information concerning the user to the emergency medical system responsive to a signal from the user requesting panic activation;

measure brain waves of the user;

transmit a signal responsive to the user touching a case of the apparatus;

request a measurement from the biometric sensor responsive to a detected predetermined motion of user;

transmit a signal responsive to the user pressing a finger against the biometric sensor;

render a medical diagnosis when in medical device mode;

render a warning of the significant detrimental change when in non-medical device mode;

use data from the plurality of biometric sensors to account for disturbances or to boost data certainty;

render substantially all data from the biometric sensor over a predetermined time period;

render the confidence level; and/or render an indication of a deviation of data from the biometric sensor from a baseline value or a population norm; etc.

The significant detrimental change can be a heart condition determined based upon a ST segment elevation.

Referring to FIG. 2, there is an example of a different type of wearable biometric apparatus 201, in the form of an armband, with multiple sensor(s) 6, which can be an ECG sensor that can be used with the preferred embodiment. Apparatus 201 can comprise an electronic area 14 that can comprise a minimal processor sufficient to govern the aforementioned process or transmit to another apparatus and/or primary processor, a wireless transmitter and/or wired connectivity to the primary processor, and a power supply large enough to power these items, for the purpose of handling input signals from the various biometric sensors, such as sensor(s) 6, and any other systemic reasons. While an embodiment need not necessarily take on this form, multiple small ECG electrodes can strike a balance between maximizing ECG signal (due to the surface area covered), and minimizing noise (due to the small size); however, such embodiments can add to the cost of the apparatus. Apparatus 201 is shown with ECG electrodes surrounding the inside of the armband. Having sensors farther apart from each other, such as above and below the arm can provide a better signal than if the sensors were placed more closely together. In addition, due to the number of sensors used in a tight proximity, it is possible to vectorize the electric signal and get directionality of the signal, which may yield even more useful data. Apparatus 201 and sensor(s) 6, as well as other sensors and embodiments, can be made somewhat stretchable and elastic, while remaining in connection with internal circuitry, as to permit more active embodiments. Apparatus 201 can of course be made of other sensors and combinations of sensors.

Referring to FIG. 3a and FIG. 3b, there is another exemplary embodiment in the form of apparatus 301, which are eyeglasses. FIG. 3a shows a front view of a person wearing eyeglasses as shown with sensor(s) 6 existing in multiple places such as on either side of the ridge of the nose where eyeglasses nose pads typically mount a nose, and on the nasion (top of the nose), where the eyeglass bridge mounts a nose in some designs. FIG. 3b shows a side profile view of a person wearing eyeglasses with a temple 302 and a temple tip 303 of the eyeglasses clearly present. FIG. 3b only shows one side profile of apparatus 301 and that every item and use mentioned on this side profile view of apparatus 301 may exist on the other side. Apparatus 301 may have at least one sensor on temple 302, which is illustrated as sensor(s) 6, or it may have at least one sensor on temple tip 303, illustrated as sensor(s) 6 (but contacting the back of the ear and/or the side of the head). Moreover, the entire temple 302 and/or the entire temple tip 303 can act as sensor(s) 6. In most uses of apparatus 301, temple 302 contacts the temporal region of the head, and temple tip 303 contacts the back of the ear in addition to the temporal region of the head. Each aforementioned contact point, especially the temporal region, could be an excellent place to use ECG or EEG sensors, which can be used to monitor heart and also brain waves (as another biometric health factor), as well as other types of sensors. Multiple sensor(s) 6 are illustrated on the side profile view of the person wearing eyeglasses to illustrate that multiple sensors may be needed to compensate for movement, sizing, or other factors to optimize the signal. Within apparatus 301 there exists an electronic area 14 that can compromise a minimal processor sufficient to govern the aforementioned process and/or transmit to another apparatus or primary processor, a wireless transmitter and/or wired connectivity to the primary processor, and a power supply large enough to power these items, for the purpose of handling input signals from the various biometric sensors, such as sensor(s) 6, and any other systemic reasons.

FIG. 4 shows a method for steps a user may complete in order to have an engaged apparatus 401, and a method for panic activation. In certain exemplary embodiments, a user may have to complete several steps in order to have an engaged apparatus 401. If the user does not complete one or more steps, the apparatus can become a disengaged apparatus 403. An engaged apparatus 401 is one in which EMS activation can occur by using the system. A disengaged apparatus 403 is one in which communication with a call station 509 of FIG. 5a and/or EMS activation 510 of FIG. 5a will not occur when using the system (unless panic activation is initiated, but all previous steps may still take place). The apparatus may continue to perform methods via elements 501 to 508 of FIG. 5a to detect inputs and store data for observation or for later use.

To have an engaged apparatus 401, training 404 can be given to the user of the apparatus, which can comprise a brief education session of what the apparatus is capable of, how it works, and how it integrates into the system. Training 404 can occur on the apparatus, or off the apparatus, for example, on a paper brochure, or on a multimedia device (such as a smartphone, computer, web browser, etc.).

The user can then complete information input 405, where the user can input relevant health parameters such as: age, race, height, weight, allergies, prescriptions, immunizations, medical legal orders such as Do Not Resuscitate (DNR), Power Of Attorney (POA), medical health care proxy, medical directives (such as organ donation), past medical history (for example, pre-existing conditions, if the patient had surgery, in particular cardiovascular related surgery or procedures, such as a stent placed, or pacemaker, or any other history), and family history. Information Input 405 may also request a user to input their name, gender, permanent address (or address they spend most time at), and will continuously repopulate itself with the GPS coordinates and location of user. Information input 405 can be used to inform a call station with detailed medical information about the caller, which may be highly relevant to the nature of the emergency, and to adjust how the algorithm handles biometric data and calculates the confidence it assigns to its results. For example, a patient who indicates in their past medical history that they have had a myocardial infarction may cause the algorithm to allow smaller detrimental changes in health related parameters to trigger an alert, or it may boost the confidence in its findings that a significant detrimental change in health related parameters has occurred once changes are detected. In addition, the algorithm could easily make use out of data from information input such as a patient indicating a high weight and low height (a high body mass index), thus increasing the risk factors for certain conditions, such as stroke. The apparatus, or an associated primary processor, can prompt the user to update the profile they entered into information input to keep it as current as possible. While information input 405 can be inputted by the user, information input 405 can also be populated from other inputs, such as but not limited to medical records, devices such as pacemakers, internal defibrillators, smart scales, smart blood pressure, glucometers, other wearable/non-wearable biometric devices, and/or existing shared electronic medical records, etc.

Next, the user can initiate calibration 406 of the apparatus, which can take a variety of forms. In the most basic form of calibration 406, the user will be asked to minimize and/or maximize movement and stay in a relaxed state for a brief period of time. The system will attempt to create baselines for each sensor. In addition, it is also possible for the system to find the differences for each sensor's data between the individual user, and the average population the patient falls into (as determined by information input). In more advanced forms of calibration 406, a user can use multiple points of their body, especially for ECG calibration, with some examples offered in FIG. 1a and FIG. 1b.

Each individual biometric apparatus needs to be calibrated for its biometric sensors to understand how to best utilize the signals, then the use of multiple biometric sensors can help to calibrate one another (you may want to get a confirmatory reading from two or more sensors). By comparing more devices together, the accuracy of each individual device can potentially be improved. At the algorithm level, the algorithm may want to determine the usefulness or the ways in which it can use a variety of biometric inputs. For example, sometimes the user may wear a varying number of apparatuses, and this may change the confidence levels for the algorithm. Calibration data can also be created by using multiple apparatuses individually and/or concurrently, it can be loaded into the apparatus from other devices, and/or it can come from sources that have past biometric data on the patient, etc. A user can be prompted for situational calibration at a later point if it becomes apparent to the system that the user may be situationally (temporarily) performing an activity that significantly changes the physiology of the user for a limited period of time, such as but not limited to intense physical activity. In some situations, situational calibration could auto-engage, for example, if the apparatus's accelerometer or gyroscope detected movement consistent with running (through the system), the system could create a calibration profile for typical health parameters of the user while running. Alternatively, a user can alert the system of an activity a user is performing, such as mountain climbing, and the user can create a health parameter profile pertaining to that activity. The more scenarios the apparatus and system experiences, the better calibrated the apparatus will become. Calibration information can be useful to the algorithm. A user can satisfactorily complete calibration 406, which will be determined by the system. For active users, one method the system can use to determine if it is calibrated, is to see if it can detect significant, but not detrimental changes in health related parameters, such as when a user runs.

Lastly, the user can complete an opt-in 407, which can take a variety of forms. In the preferred embodiment, the opt-in can comprise disclosures and disclaimers that the patient can acknowledge and accept, respectively. Depending on the patient's demographics and risk factors recorded in the information input, there may be a fewer or greater number of terms to accept. The opt-in 407 can be acknowledged or accepted in a variety of ways, such as but not limited to by opening the product, by purchasing the product at the point of sale with a signature, or by pressing a button on the apparatus in an introductory menu. Opting-in can also indicate that the user has completed training, information input, and/or calibration successfully.

In certain exemplary embodiments, the user at any time can initiate a communication with call station 509 (FIG. 5*a*) by engaging a panic activation mechanism, such as a button or gesture, signaling trouble (thus making the apparatus become engaged). Panic activation can be a tremendously useful function when a user recognizes that they are in an emergency and they need immediate attention, whether it be police, medical, fire, or another type of emergency. In the preferred embodiment, panic activation will send an alert to call station 509 (which will eventually be passed onto EMS if help is needed) with any information already registered in the apparatus' database from information input; and the apparatus will initialize the detection of health parameters (if not already initialized), and make available known health information and parameters to the call station (and the EMS) in real time, so that the EMS can be best prepared to respond to the emergency—a vast improvement over prior art.

Referring to FIG. 5*a*, there is a flowchart of system 500, which details the system that occurs on the biometric apparatus, externally on the primary processor, and outside of both the biometric apparatus and primary processor (for example, the call station 509). The biometric apparatus starts by using at least one sensor(s) 501 to detect a health parameter. The information gathered from the sensor(s) 501 is then amplified and filtered at 502. Amplification and simple filtration 502 might not necessarily happen in a strict order, as the exact process of amplification and filtration can vary from sensor to sensor, or for a multitude of reasons to optimize certain embodiments. Information can be converted from an analog state to a digital state using analog to digital converter 503. Elements 502, and 503 may be interchangeable depending on the technical requirements of 501, 502 and/or 503. Elements 501-503 can be comprised by the biometric apparatus, because they require little to no computational power, and a minimal amount of energy. In the spirit of optimizing energy usage on the biometric apparatus and maximizing processing power, digital signals are then communicated to the primary processor from the biometric apparatus in order to undergo signal processing 504. Communication outputs of 502 and/or 503 to the primary processor system input of 504, can happen via any means, such as wired, or wireless, as previously described in the summary.

Signal processing 504 can vary from a complex to a simple process, depending on how noisy the signal is that was originally picked up by sensor(s) 501, and can use, but is not limited to, any mathematical or statistical tools mentioned in the summary and later further described. Multiple arrows are illustrated to show independent sources of data, and how those data outputs may be separated (except in the event where one of the sources of data combines information to create a new source of data), until they all get inputted to algorithm 505. For example, an ECG sensor on the apparatus will be independently amplified, filtered, A/D converted, and signal processed (except in the event where one of the sources of data combines information to create a new source of data), until its data gets merged into the algorithm where a decision is made. Each sensor can have its own process of sensing from items 501-504.

Algorithm 505 occurs on the primary processor and is responsible for compiling all of the data streams from signal processing 504 (also on the primary processor), and making a determination as to whether or not a significant detrimental change in health parameters have been detected 506. While the algorithm may be capable of making a specific diagnosis, for the purposes of simply detecting an emergency, the preferred embodiment will only detect the occurrence of significant detrimental changes, which is far easier to detect than where or what the specific problem is. There are a nearly limitless number of scenarios that can be classified as "significant detrimental changes." Having the knowledge that a significant detrimental change in a health parameter has occurred is an excellent reason to seek medical attention.

Algorithm 505 may operate by analyzing snapshot(s) 515 of biometric data (of varying lengths), comparing the snapshot(s) 515 to decide if a significant detrimental change in health related parameters has occurred, and also by considering data from information input 1005 of FIG. 10 (as previously described). A snapshot 515 (see FIG. 5*b*) is a portrayal of data in a moment of time. Database 514 (see FIG. 5*b*) may store and retrieve snapshot(s) 515 (see FIG. 5*b*) for use by algorithm 505.

With an ECG, changes in the amplitude of the QRS complex (the voltage potential) as well as prolongation (time) of the complex from one time point to another could be indicative of alarming developments in the heart. ST segment elevation, a sign for ST segment elevation myocardial infarction (STEMI), can be recognized by comparing normal baseline patient data to new information, which by comparison, may show ST elevation. On the other hand, ST depression may indicate the possibility of a stroke. Additional examples of changes that can be observed with an ECG are detailed later, within FIG. 6. With a pulse oximeter or laser Doppler flowmeter, changes in pulse or oxygen saturation could indicate other causes for alarm, especially when corroborated with data from other sensors.

If no significant detrimental changes in health parameters have been detected, nothing is done at element 507, which means the system continues to function in its normal state without issuing an alert 508. If a significant detrimental change in health parameters is detected, then an alert 508 is issued by the primary processor unit, which can express itself through the biometric apparatus, or through any means accessible to the primary processor. The alert can take on multiple embodiments, including but not limited to: vibrating, flashing with vibrant lights (such as but not limited to a red and blue strobe light), displaying text or graphics, or initiating phone calls, text messages, pagers, or other modes of communication. The intent of alert 508 is to capture the user's attention, surrounding people's attention, and distant parties who have the patient's consent to be informed (family, caregivers, and/or health professionals, etc.). Depending on the circumstance, which will be detailed later, call station 509 will be contacted which can initiate EMS activation 510. Alternatively, for any reason, the patient can initiate panic activation 408 and get the attention of the call station immediately without any algorithmic assistance. EMS Activation 510 implies that help is on the way be it medical, fire, police, or another emergency agency, or that the patient has been appropriately advised how to handle the emergency (for example through two-way communication).

Call station 509 can take on a variety of forms including a government service, like a 911 dispatcher, a non-government service, such as an alarm company, or a health care professional directly. Communication from the apparatus to the call station can include but is not limited to any data from elements 501-508, information input 405, and a video and/or audio link from the preferred embodiment. A preferred embodiment may have a live audio link and/or a live video link from the call station to the patient while the emergency is happening to efficiently activate EMS, council the patient, and find out as much relevant information as possible.

Referring to FIG. 5b is system 500, which is a magnification, extension, and elaboration of system 500 that exists from elements 505-510 on FIG. 5a. The algorithm 505 utilizes stored and retrieved information from a. database 514. Data stored from the primary processor can be housed in database 514.

After Algorithm 505 determines that there has been a significant detrimental change in health parameters detected 506, the system determines if prohibiting factors apply 511. A prohibiting factor can be either user initiated for any reason, or it can be automatically determined. An example of a prohibiting factor could be a patient wanting to disable the device or system for privacy reasons. Another example could be that the patient lives with a chronic illness that will routinely set off alert 508 (in this case, the prohibiting factor could be selective for certain algorithmic findings or sensors). A prohibiting factor will cause the device to do nothing at element 507 if a significant detrimental change in health parameters has been detected.

If no prohibiting factors apply, alert 508 is triggered as previously described in FIG. 5a, however, depending on how high the confidence level 512 is of algorithm 505, at least two different pathways can be taken (the number of pathways may increase commensurate with how many categories of confidence there are, for example there may exist confidence levels 1 through 10 each with different associated actions). If confidence is high, a communication channel is opened to call station 509. If confidence is low, the patient will be prompted with patient choice 513. The goal of the confidence intervals is two fold: first, it is valuable information that can be sent to the call station so a dispatcher will know how sure the algorithm is, which could be useful for limiting false alarms, and second, it allows the patient more opportunities to make the call themselves, rather than automating the care when someone may not feel they need to go to the hospital—it gives them some leeway of independence and control.

Patient choice 513 can provide an opportunity for a patient to respond to alert 508 in any form the apparatus or primary processor will allow, such as by making a selection on the apparatuses display (which can be a touch screen), by pressing button 9 of FIG. 1 or 12 of FIG. 2, or by any other means. From this point, a patient can decline help, in which case nothing further is done, a patient can request help, in which they will be put in communication with call station 509 of FIG. 5a, and if no action is taken by the patient in a short time period (perhaps indicated by display 3 of FIG. 1a), they will automatically be put in communication with call station 509 of FIG. 5a (in this last scenario, the assumption is that they are incapacitated). Through the possible two-way communication, a false alarm can still be indicated and the communication cancelled by call station 509 of FIG. 5a. Call station 509 of FIG. 5a will review the data presented from the apparatus and system, and will make a determination with the patient whether or not to initiate EMS activation 510. In some embodiments, call station 509 of FIG. 5a can be skipped in its entirety, and EMS activation 510 can occur directly. It can again be seen in FIG. 5b as it was in FIG. 5a, that if the patient engages panic activation 408, the patient will immediately be placed in communication with call station 509 of FIG. 5a with a plethora of useful information provided to dispatchers from the apparatus and system. It should be apparent that omissions or deviations from the systems, methods, processes, and apparatus mentioned in this patent that have the same spirit will still be considered within the scope of this patent.

Using a heart sensor, such an ECG, the apparatus can detect the electrical activity of the heart over time. FIG. 6 is a graphical representation of illustrative electrical activity of a heart during a heartbeat. Representation 600 may include a plot of the variation of the heart's electrical potential over time. A typical heartbeat may include several variations of electrical potential, which may be classified into waves and a complex. For example, representation 600 can include P wave 601, QRS complex 602, and T wave 603. Some representations can in addition include a U wave (not shown). The P wave can represent normal atrial depolarization, when the main electrical vector spreads from the right atrium to the left atrium. The shape and duration of the P wave can be related to the size of the user's atrium (e.g., indicating atrial enlargement).

The QRS complex can correspond to the depolarization of the heart ventricles, and can be separated into three distinct waves—a Q wave, an R wave, and an S wave. Because the ventricles contain more muscle mass than the atria, the QRS complex is larger than the P wave. In addition, the His-Purkinje system of the heart, which can increase the conduction velocity to coordinate the depolarization of the ventricles, can cause the QRS complex to look "spiked" rather than rounded. The duration of the QRS complex of a healthy heart can be in the range of approximately 60 to approximately 100 milliseconds ("ms"), but can vary due to abnormalities of conduction.

The duration, amplitude, and morphology of each of the Q, R and S waves can vary significantly for users having cardiac diseases or cardiac irregularities. For example, a Q wave that is greater than ⅓ of the height of the R wave, or greater than approximately 100 ms in duration can be indicative of a myocardial infarction.

Representation 600 can include a PR interval 604 and ST segment 605. PR interval 604 can be measured from the beginning of P wave 601 to the beginning of QRS complex 602. PR interval 604 can typically last approximately 120 to approximately 200 ms. PR interval 604 having a different duration can indicate one or more defects in the heart, such as a first degree heart block (e.g., PR interval 604 lasting more than approximately 200 ms), a pre-excitation syndrome via an accessory pathway that leads to early activation of the ventricles (e.g., PR interval 604 lasts less than approximately 120 ms), or another type of heart block (e.g., PR interval 604 is variable). ST segment 605 can be measured from QRS complex 602 to T wave 603, for example starting at the junction between QRS complex 602 and ST segment 605 and ending at the beginning of T wave 603. ST segment 605 can typically last from approximately 80 to approximately 120 ms, and normally has a slight upward concavity.

T wave 603 can represent the repolarization or recovery of the ventricles. The interval from the beginning of the QRS complex to the apex of the T wave can be referred to as the absolute refractory period. The last half of the T wave can be referred to as the relative refractory period or vulnerable period.

QT interval 606, which can represent the total time needed for the ventricles to depolarize and repolarize, can be measured from the beginning of QRS complex 602 to the end of T wave 603. QT interval 606 can typically last between approximately 300 and approximately 1050 ms, and can vary based on the condition of the user's heart rate. Several correction factors have been developed to correct QT interval 606 for the heart rate.

Referring to FIG. 7, system 700 shows wearable apparatus 1 (watch embodiment) and/or apparatus 301 (eyeglasses embodiment) in communication with primary processor 702 (smartphone) and/or primary processor 701 (cloud/network based service), as well as with each other, in any combination, for any purpose, in any wired or wireless communication medium available. In this embodiment, primary processor 701 is a cloud/network service, or a remote computer of some sort, and primary processor 702 is a smartphone, or some other device that can remain near the user, but has significantly larger processing and energy parameters than a wearable apparatus, as they will be receiving offloaded signals for analysis and processing by the algorithm to make a determination as to whether significant detrimental changes in health parameters have occurred that would necessitate EMS activation.

System 700, can relate to any primary processor, or any apparatus, that is within the scope and spirit of this application. In addition, two primary processing units 701 and 702, and two apparatuses 1 and 301, are shown in FIG. 7 as an example of how it is also possible to have two or more apparatuses and/or two or more primary processors as part of system 700. In the most basic embodiment, it is possible to use only one apparatus to initiate panic activation 408 (FIG. 5a), regardless of the use of any biometric sensor(s) 6, which is an improvement over prior art.

Referring to FIG. 8 graph 800, which shows an embodiment of how signal processing 504 can be carried out. Graph 800 illustrates a hypothetically noisy ECG signal over time, before signal processing 504, which is not immediately distinguishable (as a result of the noise). However, certain points with a high level of confidence may be distinguishable, such as distinguishable point 802, as well as other points circled. In this example, distinguishable point 802 is also an example of part of a P wave 601 from FIG. 6. These points are remembered by the primary processor and are analyzed with the expectation that the ECG should have characteristic signature components that relate to FIG. 6, for each heartbeat.

The preferred embodiment for reaching higher confidence in distinguishability would employ a method to average results over time to see where different voltage points cluster around a model of one heartbeat 801. It is more likely that points that cluster more often represent true points on the ECG, and are not noise artifacts. Every heartbeat provides a chance to integrate more data, and to refine and/or iteratively save a snapshot 515 of FIG. 5 of a model of one heartbeat 801 that is being constructed to later compare and find moment-to-moment changes (retrieved from database 514 of FIG. 5).

Distinguishable point 802 is then extracted from the noisy graph 800, and becomes distinguishable point 803 (circled), which is placed among other distinguishable points (also circled on model of one heartbeat 801), in order to build an averaged model of one heartbeat 801, which is the patient's current ECG averaged over multiple heartbeats condensed into one beat. Time point R 806 and time point S 807 (for example 10,000 and 13,000 milliseconds, respectively, which represent three heartbeats at 60 beats per minute), are illustrated in graph 800. Time point M 808 and time point N 809, which will always represent how long one beat takes from start to end, respectively (for example 0 and 1,000 milliseconds, respectively, which represent one heartbeat at 60 beats per minute), are illustrated in model of one heartbeat 801. Depending on the clarity of the signal input from elements 501-503 of FIG. 5a, and the success of signal processing 504 of FIG. 5a to create suitable information for algorithm 505 of FIG. 5b, time point R 806 and time point S 807 may differ significantly from the example, and are dynamic. From all of the gathered points with high confidence, it is relatively easy to make accurate assumptions as to how the pieces are connected, if an entire ECG cannot be constructed. Points 805 represent the assumed data points that connect distinguishable points 803 together and form a complete ECG model of one heartbeat 801, but can not be clearly distinguished from graph 800. In certain exemplary embodiments, signals from other sensors (e.g., pulse oximeters, etc.) can be acquired over a length of time and averaged, and/or areas of high confidence can be distinguished, stored, and analyzed and processed in an analogous manner to the illustrated ECG signal.

Graph 800 is illustrative of how algorithm 505 of FIG. 5b uses model of one heartbeat 801 as a snapshot 515 of FIG. 5b from a point in time to compare to other stored snapshot(s) 515 of FIG. 5b of model of one heartbeat 801 from different points in time.

The time interval a snapshot 515 of FIG. 5b covers can change significantly and dynamically as dictated by signal processing 504 of FIG. 5a and algorithm 505 of FIG. 5a. Snapshot(s) 515 of FIG. 5b of time points may be compared to each other to determine moment-to-moment changes, snapshot(s) 515 of FIG. 5b may be compared to the baseline established in calibration 406 of FIG. 4, snapshot(s) 515 of FIG. 5b may be compared to recognized population norms (or recognized population norms for detrimental conditions) which may also be stored as snapshot(s) 515 of FIG. 5b, and if available, snapshot(s) 515 of FIG. 5b may be compared to previous snapshot(s) 515 of FIG. 5b taken in the past around the events leading up to (and including) when alert 508 of FIG. 5b was triggered. Whether a snapshot 515 of FIG. 5b is calculated or determined to be significantly similar to a snapshot 515 of FIG. 5b containing detrimental changes in health parameters, or whether a snapshot 515 of FIG. 5b is calculated or determined to be significantly different from a baseline snapshot 515 of FIG. 5b, algorithm 505 of FIG. 5b will trigger alert 508 of FIG. 5b, etc. Certain exemplary embodiments can also comprise other techniques similar in spirit to those described.

Those skilled in the art will notice that in this specific example illustrated in FIG. 8 of model of one heartbeat 801, the patient appears to be having a ST elevation myocardial infarction ("STEMI") (an example of a detrimental health state), which is especially noticeable in Region 811. Region 811 shows ST elevation. Element 810 is an area of graph 800 was ruled to be "true" and was used to construct a representative heartbeat for 801

Referring to FIG. 9 is set of graphs 900, which shows another embodiment of how signal processing 504 of FIG. 5a can be carried out. Graph 901 shows a photoplethysmogram (PPG), which can be obtained by using a pulse oximeter, a laser Doppler flowmeter, and/or a similar sensor, etc. Graph 800 from FIG. 8 again illustrates a hypothetically noisy ECG signal from time point R to time point S, before signal processing 504 of FIG. 5*a*, which is not immediately distinguishable (as a result of the noise). Graph 902 is a reconstructed ECG from techniques described below.

In the preferred embodiment, it is particularly useful to combine two or more types of sensors, to yield more accurate data. The combination of ECG and PPG sensor data can yield especially useful information. In terms of PPG sensor data, it is well known that the time distance from first PPG peak 903, to second PPG peak 904 is known as the peak-to-peak time of the PPG, and is highly correlated to the duration of a heartbeat. There have been several advancements in recent years to improve a PPG's ability in detecting heart rate, such as Sun, et. al [1].

The duration of a heartbeat is generally considered to be the time between R wave peak 905, and consecutive R wave peak 906. In the event that the ECG is noisy, which is the case in graph 800, the distance between R wave peak 905 and R wave peak 906 can be accurately extrapolated by easily measuring the distance between PPG peaks 903 and 904 (based on their overlapping and known offset alignment, relative to one another). This is valuable information because an algorithm can look for the R waves (the most detectable part of an ECG due to the greatest amplitude) within graph 800 that correspond with the period that was determined from PPG peak 903 and PPG peak 904, which will assist signal processing 5010 of FIG. 5*a*. In addition, as the electrical signal of the heart (detected by the ECG) creates the mechanical phenomena of the heart pushing blood (as detected by PPG), it is known that R wave peak 905 will precede PPG peak 903. However, because of this phenomenon and the periodicity of a heartbeat, it is important to point out that R wave peak 906 will occur between PPG peaks 903 and 904, and in addition, R wave peak 906 will precede PPG peak 904, which greatly assists signal processing 504.

Combining signal processing techniques, where applicable, can improve the signal to noise ratio, and the ability of signal processing 504 and algorithm 505 of FIG. 5*a* to determine if a significant detrimental change in health related parameters has occurred. In many ways, signal processing 504 and algorithm 505 of FIG. 5*a* work synergistically together, where signal processing 504 and algorithm 505 of FIG. 5*a* can dynamically interchange their process order, for example signal processing 504 may occur first, and then algorithm 505, or alternatively algorithm 505 may occur first and then signal processing 504 can follow, as illustrated in FIG. 5*a* and FIG. 5*b* with bi-directional arrows between signal processing 504 and algorithm 505. Furthermore, other signal processing techniques may be used to achieve the same spirit of the application.

The techniques illustrated in set of graphs 900 and graph 800 can be applied to data retrieved from any type of biometric sensor (such as a laser Doppler flowmeter, pulse oximeter, etc.), not just an ECG sensor, or the respective sensor discussed in the detailed description of the application, or any other type of sensor.

FIG. 10 is a block diagram of an exemplary embodiment of an information device 10000, which in certain operative embodiments can comprise, for example, electronic area 14 of FIG. 1*a* and/or peripheral devices coupled thereto. Information device 10000 can comprise any of numerous circuits and/or components, such as for example, one or more network interfaces 10100, one or more processors 10200, one or more memories 10300 containing instructions 10400, one or more input/output (I/O) devices 10500, and/or one or more user interfaces 10600 coupled to I/O device 10500, etc.

In certain exemplary embodiments, via one or more user interfaces 10600, such as a graphical user interface, a user can view a rendering of information related to user health information and/or any of the products, services, methods, and/or information described herein.

FIG. 11 is a flowchart of an exemplary embodiment of a method 11000. At activity 11100, an apparatus wearable by a user can be produced. The apparatus can comprise:

a biometric sensor;

a signal filter constructed to average signals from the biometric sensor; and/or a wireless transmitter/receiver constructed to:

receive information concerning an established confidence interval for the averaged signals; and/or receive information concerning predicted timing of a signal from the biometric sensor based upon a pulse oximeter obtained via one or more of:

the pulse oximeter of the user bounded by a QRS complex; and/or electrical waves of the QRS complex in consideration of information from a photoplethysmogram.

At activity 11200, the apparatus can be activated, such as with an emergency medical system. At activity 11300, via information obtained from a motion sensor, movements of a body part of the user can be compensated for.

At activity 11400, snapshots can be compared, such as via a processor. A snapshot of a model of a heartbeat of the user obtained from the biometric sensor can be compared with a recognized population norm to decide if a significant detrimental change in health related parameters has occurred. A snapshot of a model of a heartbeat of the user obtained from the biometric sensor can be compared with a previous snapshot obtained from the user to decide if a significant detrimental change in health related parameters has occurred.

At activity 11500, data can be transmitted, such as via a wireless transmitter/receiver. For example, data can be transmitted from the biometric sensor at a predetermined time after a prior transmission. Data can be transmitted from the biometric sensor responsive to a determination that a count of readings from the biometric sensor exceeds a predetermined threshold. Compressed data can be transmitted from the biometric sensor.

At activity 11600, data can be received, such as via a wireless transmitter/receiver. For example, a request can be received from a processor for data required to reconstruct an accurate snapshot. The request can be based upon an analysis of minimal received data and a determination that the minimal received data is insufficient to reconstruct the accurate snapshot.

Certain exemplary embodiments can comprise requesting snapshot information stored in a database. Certain exemplary embodiments can comprise, via information obtained from a motion sensor, compensating for movements of a body part of said user.

WORKS CITED

Xuxue, S., et al. Robust heart beat detection from photoplethysmography interlaced with motion artifacts based on Empirical Mode Decomposition. Biomedical and Health Informatics (BHI), 2012 IEEE-EMBS International Conference on, (2012).

Definitions.

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

account—to determine a cause.

accurate—substantially consistent with an actual value.

activate—to register with.

activity—an action, act, step, and/or process or portion thereof.

adapted to—made suitable or fit for a specific use or situation.

adapter—a device used to effect operative compatibility between different parts of one or more pieces of an apparatus or system.

against—into contact with.

algorithm—a set of rules followed in determinations.

analysis—determining one or more features of something via careful examination.

analyze—to examine carefully and in detail.

and/or—either in conjunction with or in alternative to.

apparatus—an appliance or device for a particular purpose.

arm—each of the two upper limbs of the human body from the shoulder to the hand.

associate—to join, connect together, and/or relate.

automatically—acting or operating in a manner essentially independent of external influence or control. For example, an automatic light switch can turn on upon "seeing" a person in its view, without the person manually operating the light switch.

average—to smooth a signal in a manner such that the signal magnitude approximates a mean of a plurality of signal values.

average population—a large number of people that in some sense are representative of a user.

backbone network—a "transit" network often made up of long-distance telephone trunk lines and/or other wired and/or wireless links such as microwave and satellite links for use in transmitting large amounts of data simultaneously between host computer systems connected to the Internet. Normal communicated data typically neither originates nor terminates in a backbone network.

bandpass filter—an electrical circuit constructed to attenuate substantially all frequencies except those of a specific band, which it amplifies.

base—a foundation for a determination.

baseline value—a standard magnitude of a parameter.

belong—to fit in a specified category or group.

between—with reference to a differentiation involving two or more things being considered together.

biometric—constructed to measure a physical characteristic.

biometric sensor—a sensor constructed to measure a physical characteristic. Exemplary biometric sensors comprise, for example, heart rate monitor, pulse transit time sensor, pulse oximeters, temperature sensors (e.g., thermometers), galvanometers, breathalyzers, carbon monoxide (CO) sensor, blood sugar, hygrometer, altimeter, barometer, gps detector, accelerometer, gyroscope, magnetometer, EMG (electromyographic sensor), fingerprint reader, force transducer, audio sensor (e.g., microphone), proximity sensor, human velocity sensor, ambient light sensor, blood pressure sensor, flowmeters (e.g., laser Doppler flowmeters) or any combination thereof.

boost—to increase.

bound—kept within limits.

brain wave—an electrical impulse in the brain.

button—a knob or icon on a piece of electrical or electronic equipment that is pressed to operate it.

calibrate—to correlate readings of an instrument with those of a standard in order to check the instrument's accuracy.

calibration profile for health parameters—a patterned set of correlated readings for a user for a particular physically measured value.

can—is capable of, in at least some embodiments.

cancel—to signal that an event will not take place.

capacitive—constructed to measure capacitance of a part of a human body.

capture—to obtain.

case—a container constructed to hold something.

cause—to bring about.

certainty—the state of being statistically confident.

change—to become different.

charging mechanism—an electrical circuit constructed to provide electrical energy to a battery system.

circuit—an electrically conductive pathway and/or a communications connection established across two or more switching devices comprised by a network and between corresponding end systems connected to, but not comprised by the network.

communicate—to exchange information.

compare—to determine differences between two or more things.

compensate—to adjust for something.

compress—to apply a compression algorithm to electronic data so that the electronic data takes up less space when stored on a memory device.

comprising—including but not limited to.

concerning—pertaining to.

confidence interval—a statistical interval estimate of a population parameter.

confidence level—where confidence intervals are constructed across many separate data analyses of repeated experiments, the proportion of such intervals that contain the true value of a statistical parameter.

configure—to make suitable or fit for a specific use or situation.

connect—to join or fasten together.

constructed to—built for a specific use or situation.

contact—to substantially directly touch.

convert—to transform, adapt, and/or change.

count—a total number of.

coupleable—capable of being joined, connected, and/or linked together.

coupling—linking in some fashion.

data—distinct pieces of information, usually formatted in a special or predetermined way and/or organized to express concepts.

database—an organized collection of data stored on a memory device.

data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.

decision tree—a tree algorithm in which the selection of each branch requires that some type of logical decision be made.

demographical information—data concerning a section of a population sharing common characteristics, such as age, sex, class, etc.

detect—to determine the existence of something.

difference—a way in which things are not the same.

define—to establish the outline, form, or structure of.

determine—to obtain, calculate, decide, deduce, and/or ascertain.

deviation—the difference between one of a set of values and some fixed value.

device—a machine, manufacture, and/or collection thereof.

disturbance—a change in measured data of a physical system.

electrocardiogram—a recording of electrical activity of a human heart.

electroencephalogram—a non-invasive method to record electrical activity of the brain along a scalp; EEG measures voltage fluctuations resulting from ionic current flows within neurons of a brain.

emergency medical system—a type of emergency service dedicated to providing medical care and/or transport to medical care.

energy—power derived from the utilization of physical or chemical resources.

entity—a person or organization that performs a function.

estimate—to calculate and/or determine approximately and/or tentatively.

extremity—a limb, such as a leg or arm or a part thereof (e.g., an ankle).

filter—a device that allows signals with certain properties, such as signals lying in a certain frequency range, to pass while blocking the passage of others.

finger—each of the four slender jointed parts attached to either hand (or five, if the thumb is included).

generate—to create, produce, give rise to, and/or bring into existence.

global positioning system—a space-based satellite navigation system that provides location and time information in all weather conditions, anywhere on or near the Earth where there is an unobstructed line of sight to four or more GPS satellites.

glucometer—a medical device constructed to determine an approximate concentration of glucose in the blood.

grip—to take a firm hold of.

group—a number of persons considered together as being related in some way.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

head—a portion of the human body located above the neck.

health parameters—a variable related to the physical well-being of a human.

heartbeat—a pulsation of the heart, including one substantially complete systole and diastole.

heart condition—a medical issue with the cardiac muscle of a human.

heart rate monitor—a system constructed to measure a frequency of heartbeats.

hydrophobic coating—a substantially water-proof covering.

indication—a degree marked by an instrument.

individually—one at a time.

information—knowledge gained through study, measurement, communication, research, and/or instruction, etc.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

install—to connect or set in position and prepare for use.

insufficient—lacking something that is needed.

intense physical activity—something that a human does that increases a heart rate by over fifty percent above a resting heart rate.

internal defibrillator—a device implantable inside the body, able to perform both cardioversion, defibrillation and pacing of the heart.

laser Doppler flowmeter—a device that uses a Doppler shift in a laser beam to measure a fluid flow velocity.

lead—an electrical connection such as a length of wire or metal pad that comes from a device.

location—a particular position.

machine instructions—directions adapted to cause a machine, such as an information device, to perform one or more particular activities, operations, or functions.

The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

may—is allowed and/or permitted to, in at least some embodiments.

measure—to ascertain an extent of.

measurement—an extent of a variable.

medical device mode—a user selectable functional state of a system that is constructed to provide a medical diagnosis and/or medical advice.

medical diagnosis—determining by examination the nature and circumstances of a diseased condition. Exemplary medical diagnoses comprise myocardial infarction, sudden cardiac death, stroke, and/or seizure, etc.

medical information—data concerning the physical health of a human.

medical legal orders—a legally binding instruction from a patient concerning medical care.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

minimal received data—information that has been determined to be substantially a smallest quantity information to perform a function.

model—a standard that can be used for a comparison.

motion—a bodily movement.

movement—an act of changing position.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

non-medical device mode—a user selectable functional state of a system that is constructed to provide medical information but not a medical diagnosis and/or medical advice.

notify—to give notice or report something.

obtain—to acquire.

pacemaker—an artificial device for stimulating the heart muscle and regulating its contractions.

packet—a discrete instance of communication.

panic activation—a manual activation of a device indicative of a medical problem being experienced by a user of the device.

partially—substantially less than totally.

past, family, and social history information—data concerning a patient's past medical history, the past medical history of the patient's family, and past and current activities involving the patient and other people.

past medical history—information concerning one or more characteristics of a patient, the characteristics comprising one or more of general state of health (e.g. excellent, good, fair, poor. Note any significant change from previous state), past illnesses (e.g. cancer, heart disease, hypertension, diabetes), hospitalizations, injuries, or accidents, surgeries, current medications, allergies, immunizations, substance abuse, diet, sleep, alternative therapies (e.g. acupuncture, massage, herbal medicine, vitamins, and chiropractic), obstetric/gynecologic history, birth history, and growth and development.

Peak-Peak interval—an elapsed time between successive peaks of a signal.

photoplethysmogram—a volumetric measurement of a human organ.

plurality—the state of being plural and/or more than one.

population norm—a standard value for a large number of people.

power supply—an energy source for a device and/or system.

predetermined—established in advance.

predict—to determine in advance.

press—to apply pressure to.

PR interval—the period, measured in milliseconds, that extends from the beginning of the P wave (the onset of atrial depolarization) until the beginning of the QRS complex (the onset of ventricular depolarization); it is normally between 120 and 200 ms in duration.

prior—preceding in time.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

profile information—data concerning a user.

project—to calculate, estimate, or predict.

prompt—a message or symbol on a user interface requesting input from a user.

provide—to furnish, supply, give, and/or make available.

pulse oximeter—an instrument constructed to measure oxygen saturation of hemoglobin in a sample of blood.

photoplethysmogram—an optically obtained volumetric measurement of an organ.

pulse wave—a kind of non-sinusoidal waveform that is similar to a square wave, but does not have a symmetrical shape associated with a perfect square wave.

P wave—an electrocardiogram pattern representing atrial depolarization, which results in atrial contraction.

QRS complex—the combination of three of the graphical deflections seen on an electrocardiogram.

QT interval—a measure of the time between the start of the Q wave and the end of the T wave in the heart's electrical cycle.

reading—a signal indicative of a measured physical value.

receive—to get as a signal, take, acquire, and/or obtain.

recommend—to suggest, praise, commend, and/or endorse.

reconstruct—to form a model of from measured data.

relay—to retransmit a signal.

remote—far apart; separable by a distance of at least one mile.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

request—to express a desire for and/or ask for.

responsive—acting in reaction to a stimulus.

run—to move swiftly on foot.

selective—characterized by careful choice.

sensor—a device that detects events or changes in quantities and provides a corresponding output, generally as an electrical or optical signal.

set—a related plurality.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

significant detrimental change—a determined difference in measured physiological values that have been determined to have an important negative consequence in human physiology.

smart blood pressure sensor—a device and/or system that measures blood pressure via a plurality of sensors.

smart scale—a device and/or system constructed to weigh a person and to wirelessly transmit a signal indicative of the measured weight.

snapshot—a measured physiological data set obtained over a predetermined time period.

standard—an object or value that bears a defined relationship to a unit of measure used for calibration of measuring devices.

store—to place, hold, and/or retain data, typically in a memory.

stroke—the loss of brain function due to a disturbance in the blood supply to the brain.

ST segment depression—a value determined by measuring the vertical distance between the patient's trace and the isoelectric line at a location approximately 2-3 millimeters from the QRS complex.

ST segment elevation—an indicator of a myocardial infarction (i.e., heart attack) determined to have occurred via a measurement of a higher than normal connection between the QRS complex and the T wave in an electrocardiogram.

submit—to present to an information device.

substantially—to a great extent or degree.

support—to bear the weight of, especially from below.

surround—to be substantially all around something.

system—a collection of mechanisms, devices, machines, articles of manufacture, processes, data, and/or instructions, the collection designed to perform one or more specific functions.

temporal region—the side of a human head posterior to the eyes.

time—a quantity measuring duration, usually with reference to a periodic process such as the rotation of the earth or the vibration of electromagnetic radiation emitted from certain atoms.

time period—an interval of time.

touch—to contact.

transmission—a conveyance of data from one location to another.

transmit—to send as a signal, provide, furnish, and/or supply.

transmitter/receiver—a system constructed to send and acquire signals.

user—a person wearing, and being monitored by, an apparatus.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

velocity—a time rate of change of position of a body in a specified direction.

via—by way of and/or utilizing.

warning—information that alerts someone of a potentially harmful condition.

wear—to have on one's body or a part of one's body.

wireless—using radio, microwaves, etc. (as opposed to wires or cables) to transmit signals.

wrist—a joint connecting the hand with the forearm of a human.

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.110, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A system comprising:

a commonly worn object capable of being worn by a user, said commonly worn object including a biometric sensor calibrated based on a physically-measured value of said user measured during a calibration period, said biometric sensor configured to measure biometric data from said user and generate one or more signals based on said biometric data, said biometric sensor is situationally calibratable based on user activity;

a transmitter housed in said commonly worn object and in communication with said biometric sensor, said transmitter configured to transmit said one or more signals from said biometric sensor; and at least one processor configured to receive said one or more signals from said biometric sensor via said transmitter, said at least one processor configured to determine whether said user has experienced a change that is a physiological and detrimental change by comparing a plurality of snapshots of one or more health parameters of said user, said one or more health parameters generated based on said one or more signals, said at least one processor configured to notify at least one of said user or an emergency medical system when it is determined that said user has experienced said physiological and detrimental change.

2. The system of claim 1, wherein:
said at least one processor is configured to determine whether said change indicates said user has fallen.

3. The system of claim 1, wherein:
said change includes a confidence interval.

4. The system of claim 1, wherein:
said comparing of said plurality of snapshots includes comparing at least one of said plurality of snapshots to a standard snapshot.

5. The system of claim 1, wherein:
said biometric sensor is situationally calibrated upon detection of said movement of said user consistent with a physical activity, and
said detection of said movement is performed via an accelerometer or a gyroscope.

6. The system of claim 1, wherein:
said biometric sensor is calibratable by a response of said user to a request to position said biometric sensor on at least two different parts of a body of said user.

7. The system of claim 1, wherein:
said at least one processor is configured to relay information concerning said change to said commonly worn object.

8. The system of claim 1, wherein:
responsive to user signals from said user, said commonly worn object is configured to calibrate said biometric sensor based on demographical and medical information received from said user, wherein a calibration includes a determination of differences between a signal of said biometric sensor and a standard.

9. The system of claim 1, wherein:
said biometric sensor is a heart rate monitor.

10. The system of claim 1, wherein:
said biometric sensor is a laser Doppler flowmeter.

11. The system of claim 1, wherein:
said biometric sensor is a capacitive sensor with two electrodes mounted on said user.

12. The system of claim 1, wherein:
said commonly worn object is configured to prompt said user to submit past medical history.

13. The system of claim 1, wherein:
said one or more health parameters includes at least one of photoplethysmogram sensor data or electrocardiogram sensor data.

14. The system of claim 1, wherein:
said commonly worn object is configured to allow said user to cancel an information transmission to the emergency medical system.

15. The system of claim 1, further comprising:
a signal filter configured to average signals from said biometric sensor.

16. The system of claim 1, wherein:
said commonly worn object prompts said user for information responsive to information from said biometric sensor.

17. The system of claim 1, wherein:
said commonly worn object is a watch.

18. The system of claim 1, wherein:
said biometric sensor is situationally calibrated upon detection of a movement of said user consistent with a physical activity of said user,
said commonly worn object is configured to create a calibration profile for said one or more health parameters of said user based upon information from said biometric sensor,
said calibration profile configured for use in situationally calibrating said biometric sensor, and
said situationally calibrating enabling said at least one processor to distinguish between said physiological and detrimental change and a physiological and not detrimental change.

19. A system comprising:
a commonly worn object capable of being worn by a user, said commonly worn object including a biometric sensor calibrated based on a physically-measured value of said user measured during a calibration period, said biometric sensor configured to measure biometric data from said user and generate one or more signals based on said biometric data, said biometric sensor is calibratable for a movement of said user consistent with a physical activity, and said detection of said movement is performed via an accelerometer or a gyroscope;
a transmitter housed in said commonly worn object and in communication with said biometric sensor, said transmitter configured to transmit said one or more signals from said biometric sensor; and
at least one processor configured to receive said one or more signals from said biometric sensor via said transmitter, said at least one processor configured to determine whether said user has experienced a change that is a physiological and detrimental change by comparing a plurality of snapshots of one or more health parameters of said user, said one or more health parameters generated based on said one or more signals, said at least one processor configured to notify at least one of said user or an emergency medical system when it is determined that said user has experienced said physiological and detrimental change.

20. A system comprising:
a commonly worn object capable of being worn by a user, said commonly worn object including a biometric sensor calibrated based on a physically-measured value of said user measured during a calibration period, said biometric sensor configured to measure biometric data from said user and generate one or more signals based on said biometric data, said biometric sensor is calibratable for a movement of said user consistent with the user performing a type of physical activity;
a transmitter housed in said commonly worn object and in communication with said biometric sensor, said transmitter configured to transmit said one or more signals from said biometric sensor; and
at least one processor configured to receive said one or more signals from said biometric sensor via said transmitter, said at least one processor configured to determine whether said user has experienced a change that is a physiological and detrimental change by comparing a plurality of snapshots of one or more health parameters of said user, said one or more health parameters generated based on said one or more signals, said situationally calibrating enabling said at least one processor to distinguish between said physiological and detrimental change and a physiological and not detrimental change, and said at least one processor configured to notify at least one of said user or an emergency medical system when it is determined that said user has experienced said physiological and detrimental change.

* * * * *